(12) United States Patent
Ezumi et al.

(10) Patent No.: US 7,960,696 B2
(45) Date of Patent: Jun. 14, 2011

(54) METHOD FOR INSPECTING AND MEASURING SAMPLE AND SCANNING ELECTRON MICROSCOPE

(75) Inventors: Makoto Ezumi, Mito (JP); Satoru Iwama, Hitachinaka (JP); Junichi Kakuta, Hitachinaka (JP); Takahiro Sato, Mito (JP); Akira Ikegami, Suita (JP)

(73) Assignee: Hitachi High-Technologies Corporation, Tokyo (JP)

( * ) Notice: Subject to any disclaimer, the term of this patent is extended or adjusted under 35 U.S.C. 154(b) by 321 days.

(21) Appl. No.: 12/238,171

(22) Filed: Sep. 25, 2008

(65) Prior Publication Data

US 2009/0084954 A1 Apr. 2, 2009

(30) Foreign Application Priority Data

Sep. 27, 2007 (JP) ................. 2007-250406

(51) Int. Cl.
*H01J 37/28* (2006.01)
(52) U.S. Cl. ...................................... 250/310
(58) Field of Classification Search .................. 250/310, 250/396 R
See application file for complete search history.

(56) References Cited

U.S. PATENT DOCUMENTS

| 5,412,209 | A | 5/1995 | Otaka et al. |
| 6,232,787 | B1 | 5/2001 | Lo et al. |
| 6,344,750 | B1 | 2/2002 | Lo et al. |
| 6,635,873 | B1 | 10/2003 | Todokoro et al. |
| 6,946,656 | B2 | 9/2005 | Ezumi et al. |
| 7,253,410 | B1 | 8/2007 | Bertsche et al. |
| 7,417,444 | B2 * | 8/2008 | Shinada et al. ......... 324/754.22 |
| 2010/0288924 | A1 * | 11/2010 | Kaito et al. ................ 250/307 |

FOREIGN PATENT DOCUMENTS

| JP | 5-151927 A | 6/1993 |
| JP | 2000-200579 A | 7/2000 |
| JP | 2000-208579 A | 7/2000 |
| WO | WO 03/007330 A1 | 1/2003 |

* cited by examiner

*Primary Examiner* — Kiet T Nguyen
(74) *Attorney, Agent, or Firm* — Miles & Stockbridge P.C.

(57) ABSTRACT

As an aspect for realizing accurate observation, inspection, or measurement of the contact hole with large aspect ratio, a method and a device to scan a second electron beam after scanning a first electron beam to a sample to charge the sample are proposed wherein the beam diameter of the first electron beam is made larger than the beam diameter of the second electron beam.

4 Claims, 23 Drawing Sheets

FIG. 2
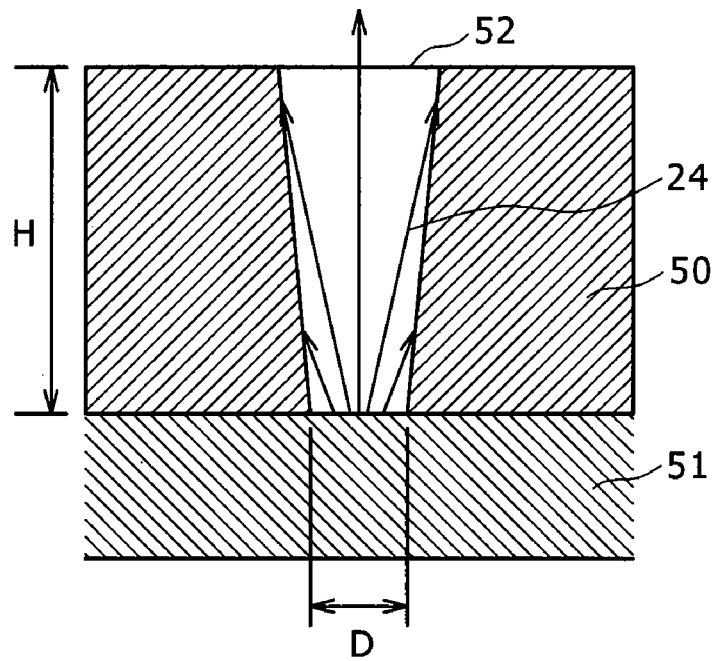
WHEN CHARGE IS NOT FORMED ON THE SURFACE
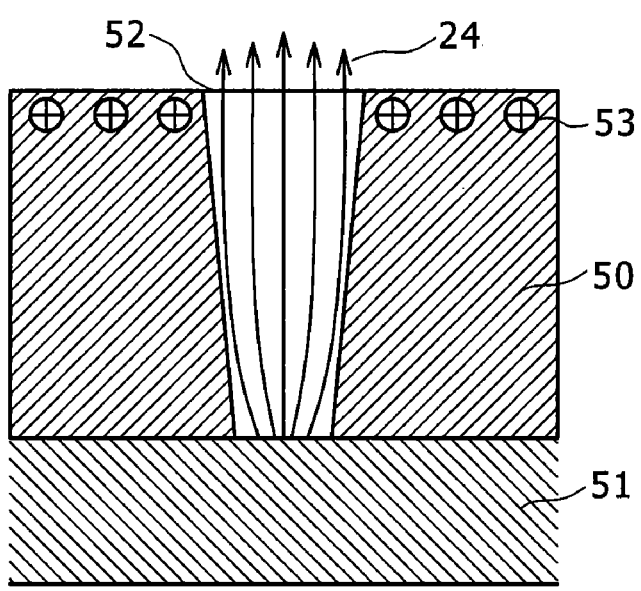
WHEN CHARGE IS FORMED ON THE SURFACE

FIG. 4
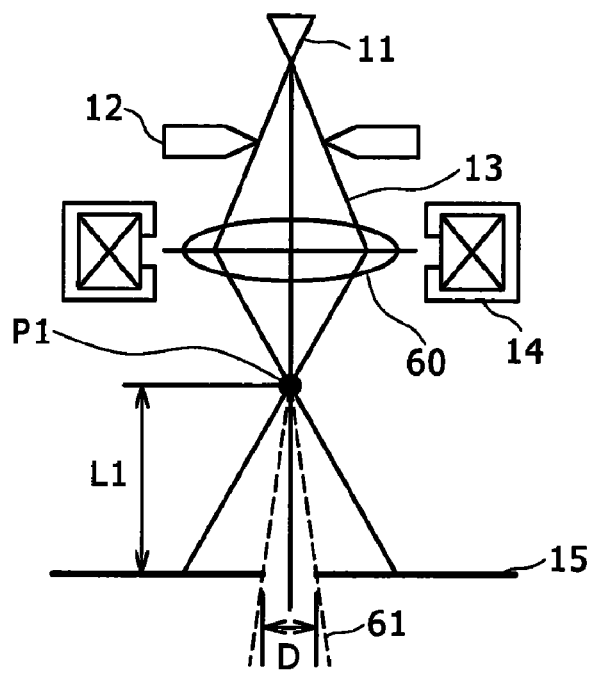
RAY DIAGRAM OF OPTICAL SYSTEM IN USUAL OBSERVATION
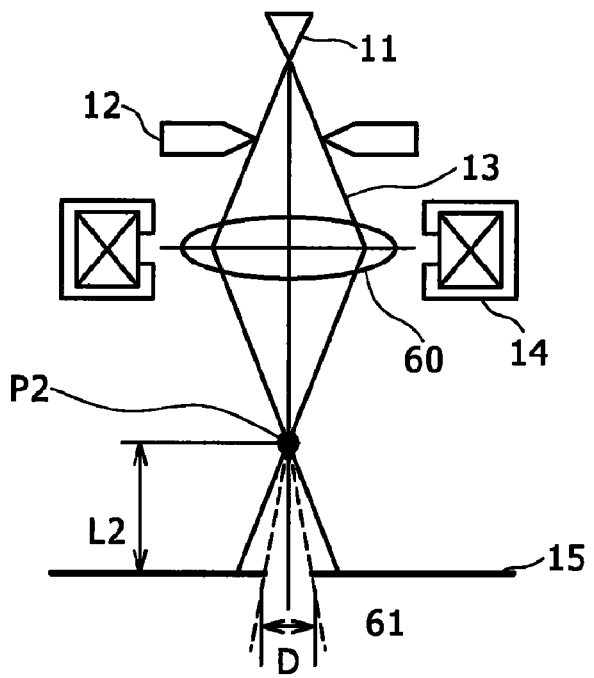
RAY DIAGRAM OF OPTICAL SYSTEM IN PERFORMING PRE-DOSE

FIG. 5
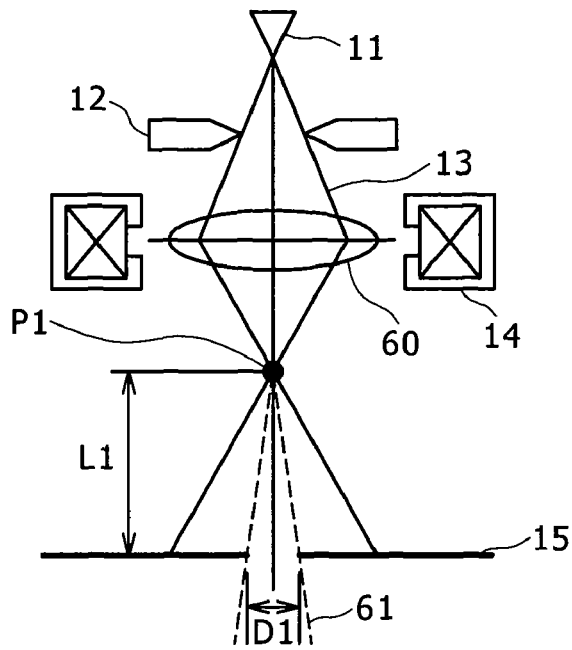
RAY DIAGRAM OF OPTICAL SYSTEM IN USUAL OBSERVATION
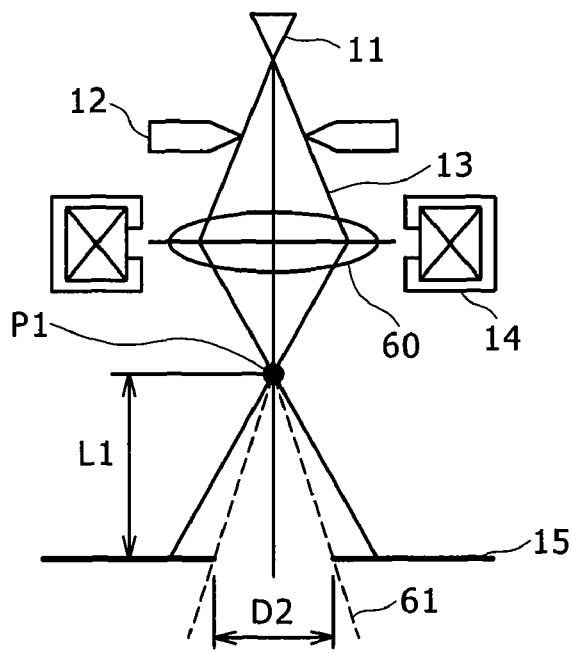
RAY DIAGRAM OF OPTICAL SYSTEM IN PERFORMING PRE-DOSE

FIG.14
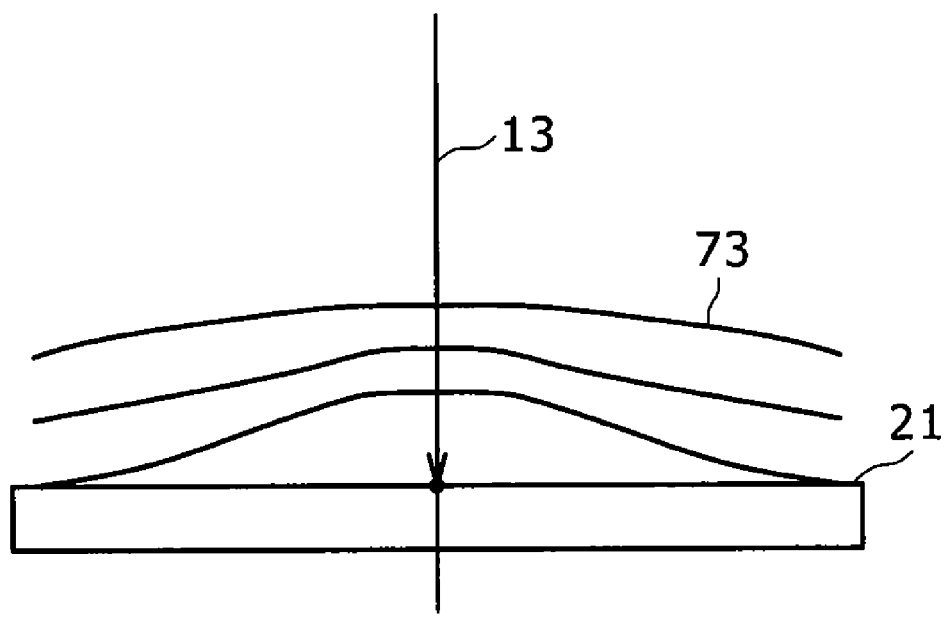
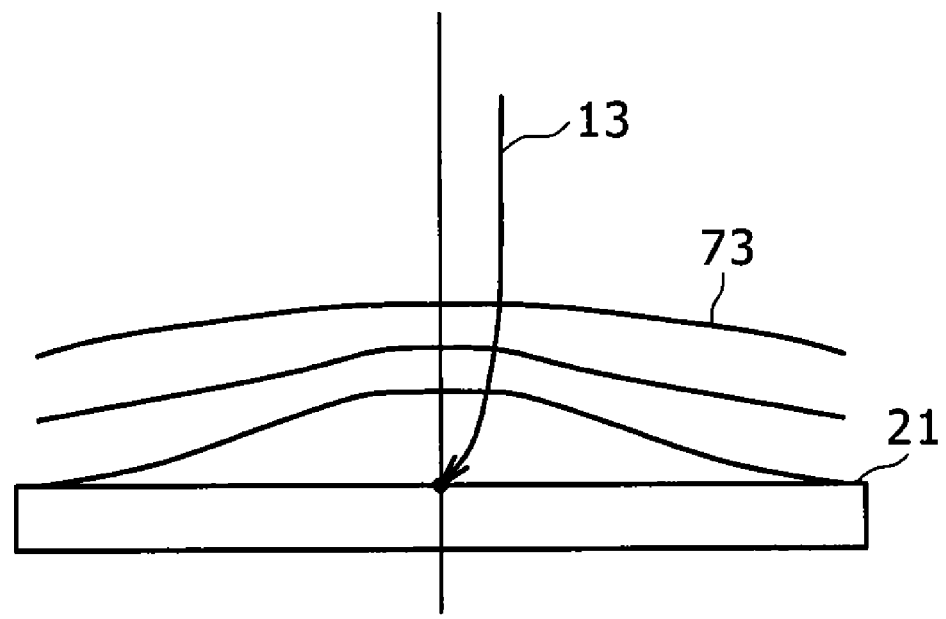

FIG.15
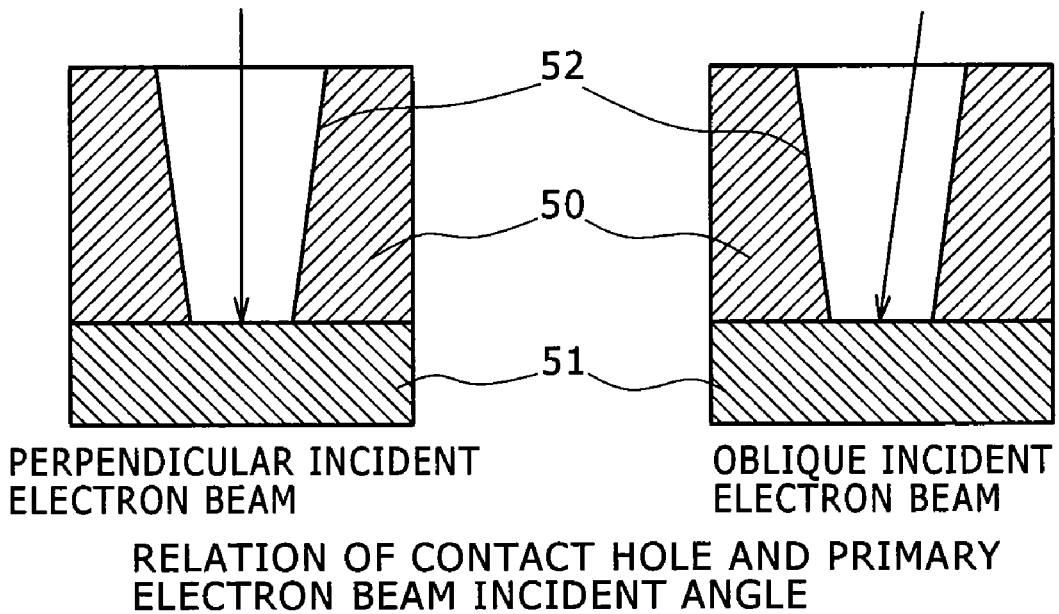
RELATION OF CONTACT HOLE AND PRIMARY ELECTRON BEAM INCIDENT ANGLE
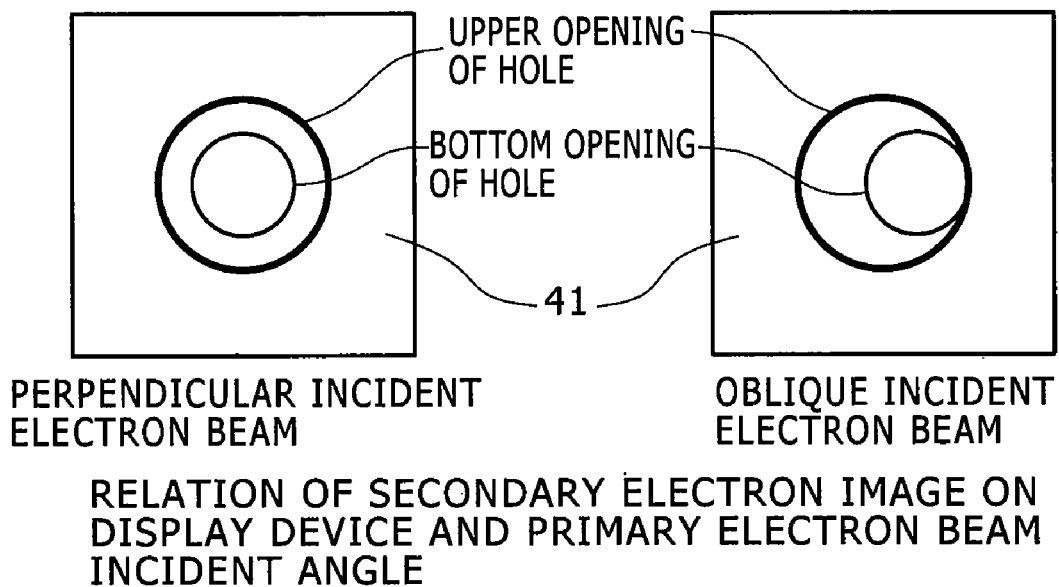
RELATION OF SECONDARY ELECTRON IMAGE ON DISPLAY DEVICE AND PRIMARY ELECTRON BEAM INCIDENT ANGLE

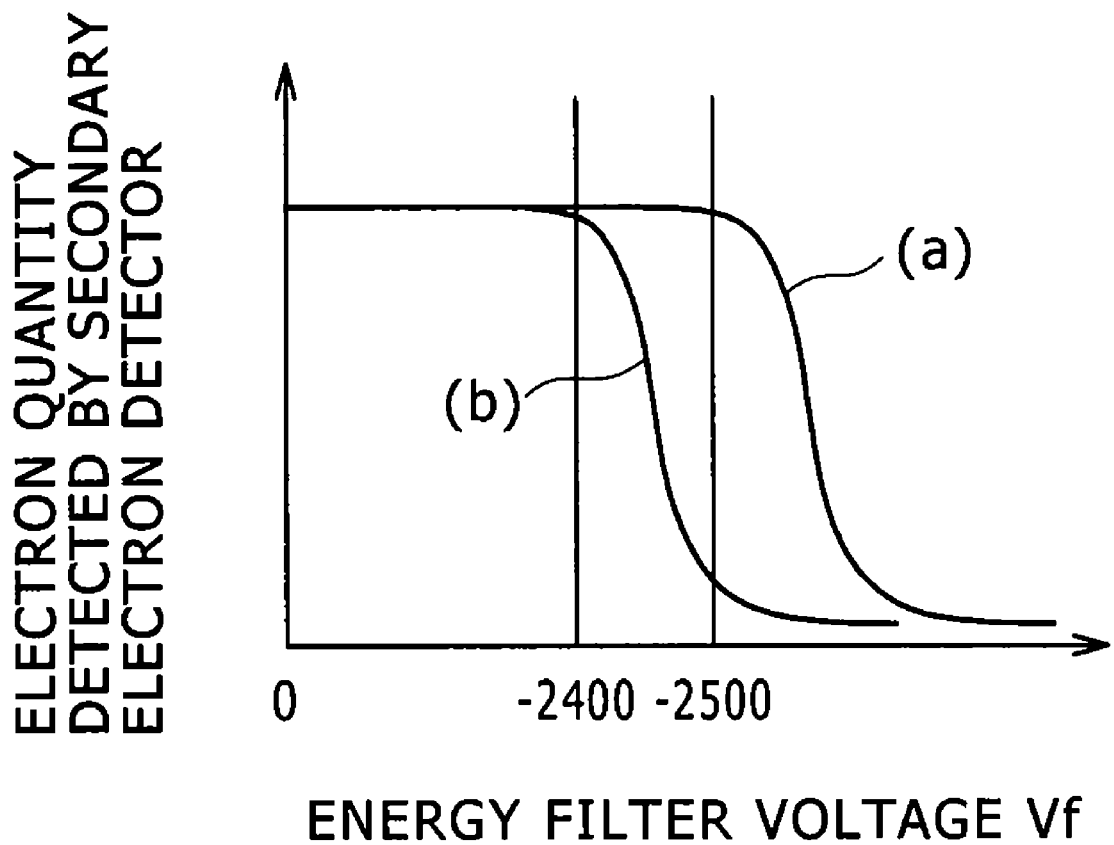

FIG. 22

| NO. | PROCESS | KIND OF INSULATION FILM | FILM THICKNESS (NM) | PATTERN SIZE (NM) | PRE-DOSE CONDITION ||||| CHARGE VOLTAGE (V) |
|---|---|---|---|---|---|---|---|---|---|---|
| | | | | | FIRST STEP ||| SECOND STEP ||| |
| | | | | | ACCELERATION VOLTAGE | IRRADIATION REGION | IRRADIATION TIME | ACCELERATION VOLTAGE | IRRADIATION REGION | IRRADIATION TIME | |
| 1 | MC | SiO2 | 1500 | 45 | 300 | 120 | 10 | 1600 | 60 | 5 | 120 |
| 2 | AEI | SiO2 | 2000 | 65 | 300 | 120 | 20 | 1600 | 60 | 5 | 150 |
| 3 | | | | | | | | | | | |
| 4 | | | | | | | | | | | |
| 5 | | | | | | | | | | | |

SELECT NO. ☐     EDIT   ADD   DELETE   CLOSE

METHOD FOR INSPECTING AND MEASURING SAMPLE AND SCANNING ELECTRON MICROSCOPE

BACKGROUND OF THE INVENTION

The present invention relates to a scanning electron microscope for inspecting and measuring a sample by scanning an electron beam to the sample, particularly to a method and a scanning electron microscope for inspecting and measuring a sample by scanning an electron beam to a sample, charging the sample, and scanning another electron beam to the sample under a charged state.

In recent years, in the light of high integration and micronization of a semiconductor element, a variety of patterns are formed on a sample (a semiconductor wafer, for example), and evaluation and measurement of their shape and size are becoming important more and more.

Particularly, in a contact hole for obtaining electric conduction between layers in multilayering, the diameter of the hole is becoming minute as micronization proceeds, and a contact hole with an aspect ratio (depth of contact hole/diameter of hole) of over 30 is not uncommon at present.

To observe and measure this contact hole, it is necessary to detect a secondary electron excited by a primary electron beam (hereinafter referred to also as electron beam), however, as the aspect ratio becomes larger, the possibility that the secondary electron collides the side wall of the hole and disappears in the hole becomes high, and as a result, there is a problem that observation and measurement of the bottom of the hole become difficult. To solve this problem, the secondary electron generated at the bottom of the hole is required to be taken out to outside of the contact hole at least.

To realize this, there is a technology (hereafter referred to also as pre-dose) that, by performing preliminary irradiation of a primary electron beam prior to electron beam scanning for inspection and measurement (hereinafter referred to also merely as observation), the region for inspection and measurement is made charge positively thereby taking out of the electron from the contact hole is facilitated.

In the patent document 1, a technology is described wherein, prior to electron beam scanning for observation, an electron beam is irradiated to wider area than that by the magnification of the time of observation (that is, by a lower magnification than that for observation) including the observation region, thereby pre-dose is realized.

Also, in the patent document 2, a technology is described wherein, prior to electron beam scanning for observation, a sample is subjected to preliminary irradiation of an electron beam whose secondary electron emission efficiency δ is larger than 1.0, the surface of the sample is charged positively, thereafter an electron beam whose secondary electron emission efficiency δ is nearer to 1.0 compared with the electron beam used for the preliminary irradiation is scanned, thereby sample observation is performed while maintaining the positively charged state stably.

Further, the patent document 3 describes that, in the relation between the magnification in preliminary irradiation and the positive charge voltage, the larger the area of preliminary irradiation, the higher the positive charge voltage which is formed on the sample.

Also, in the patent document 4, a method is described wherein, an electron emission means called flat gun, other than an electron optical system for observation and measurement, is additionally provided within the microscopy body of an electron microscope and charge is formed by overall irradiation by a large electric current.

(Patent Document 1) Japanese Published Unexamined Patent Application No. H5-151927 (corresponding to the U.S. Pat. No. 5,412,209)
(Patent Document 2) Japanese Published Unexamined Patent Application No. 2000-200579 (corresponding to the U.S. Pat. No. 6,635,873)
(Patent Document 3) WO03/007330 (corresponding to the U.S. Pat. No. 6,946,656)
(Patent Document 4) Japanese Published Unexamined Patent Application No. 2000-208579 (corresponding to the U.S. Pat. No. 6,232,787)

SUMMARY OF THE INVENTION

In recent years, because of further micronization of semiconductor devices, contact holes with large aspect ratio are formed, and it is necessary to form higher charge than before for its observation and measurement, which in turn requires to secure a larger irradiation region of the electron beam for pre-dose than before. However, if the irradiation region is enlarged, there is a problem that it takes substantially long time before the charge is stabilized.

Existence of the region not irradiated by the beam between scanning lines is considered to be its reason. Movement of the electric charge between the position the beam for pre-dose was irradiated and the position not irradiated and accompanying variation of charge quantity within the irradiated region are considered to be the reasons of the variation of the charge. If the number of scanning lines remains unchanged, the larger the irradiated region of an electron beam, the larger the non-irradiated region, and its harmful effect becomes conspicuous.

Also, lowering of electron density of the primary electron beam when the irradiated region is enlarged may possibly be the reason. Charge is determined by the continuous balance between the incident quantity of the electron beam and the emission quantity of the secondary electron from the sample, and stability of charge means the state wherein this balance becomes 1.0 practically. Accordingly, as the electron density of the electron beam lowers, the time required until the charge is stabilized inevitably becomes longer.

Further, because the electric potential is different between the center of pre-dose region and the peripheral part and the potential gradient is formed, drift of the electron beam may possibly occur.

In the patent documents 1, 2 and 3, measures against such problems are not taken at all.

Also, as is described in the patent document 4, it might be possible to make the surface of the sample be charged by overall irradiation by a flat gun, the flat gun can only irradiate to the irradiation region which covers considerably larger area than the field of view (FOV) of an electron microscope, therefore it might be possible that the charge affects even to the region not related to observation and measurement.

Moreover, if electrons are to be supplied selectively to a limited region including FOV, an optical element such as a lens or an aligner equivalent to an electron microscope becomes required. Further, because the flat gun is required to be fixed so that the electrons are supplied from a direction different from the light axis of the electron beam (here, out of the orbit where the electron beam of the electron microscope can pass) due to a physical restriction, there is also a problem that maintaining uniformity of charge within the irradiation region at a high level becomes difficult.

With respect to the charge formed on the sample, it is necessary to maintain intra-face uniformity of the charge highly precisely and the region of observation and the center of the charge should coincide, however maintaining intraface uniformity highly precisely is difficult because of the configuration that electrons are supplied from a direction different from that of the light axis of an electron beam.

Further, if an optical element different from an optical system of an electron microscope is to be arranged aiming highly precise irradiation by the flat gun, it becomes a noise source against the electron beam of the electron microscope, therefore it becomes a cause of the shift of the position of the beam for observation and measurement and increase of the beam diameter, and becomes a factor inhibiting high resolution or highly precise measurement.

Below, a method and a device for realizing highly precise observation, inspection or measurement of a contact hole with large aspect ratio will be described.

As one aspect for achieving the purpose described above, in a method and a device wherein, after a sample is charged by scanning a first electron beam to the sample, a second electron beam is scanned for observation, inspection or measurement of the sample, a method and a device is proposed wherein the beam diameter of the first electron beam is made larger than the beam diameter of the second electron beam.

According to such technique and configuration, pre-dose is performed using an electron beam with a beam diameter larger than that of the second electron beam, therefore variation of charge originated to existence of the region not irradiated by a beam can be inhibited. The second electron beam is the electron beam for inspection and measurement, and it should be extremely narrowed to improve the spatial resolution of the device. On the other hand, if the electron beam is narrowed in pre-dose, the region not irradiated by a beam is enlarged as described above. Accordingly, by enlarging the beam diameter of the electron beam in pre-dose compared with the beam for observation and the like, the region not irradiated by a beam described above can be reduced or eliminated, which enables inhibiting of variation of charge in pre-dose.

Also, as another aspect for achieving the purpose described above, in a method and a device wherein, after a sample is charged by scanning an electron beam to the sample, another electron beam is scanned for observation and the like, a method and a device is proposed wherein, in charging the sample, firstly, an electron beam whose secondary electron generation efficiency δ1 is larger than 1.0 is scanned to the region having a first magnitude, and secondly, another electron beam whose secondary electron generation efficiency δ2 is smaller than said δ1 is scanned to a region narrower than the first magnitude, thereafter an electron beam is scanned and inspection or measurement of the sample is performed.

According to such configuration, observation and the like becomes possible under uniformed charge condition.

Further, as further other aspect applying the pre-dose technology, by shiftingly forming the charge region with respect to the observation region, oblique irradiation of an electron beam becomes possible.

According to one aspect described above, quick stabilizing of the charge in pre-dose becomes possible, and as a result, realization of speeding-up of observation and the like becomes possible. Also, according to another aspect described above, realization of high accuracy measurement based on uniformed charge within the electron beam scanning region becomes possible. Further, according to further other aspect described above applying the pre-dose technology, realization of observation by an oblique beam becomes possible while inhibiting an aberration formed by a lens.

BRIEF DESCRIPTION OF THE DRAWINGS

FIG. 2 is a drawing showing shape of a contact hole formed on a wafer and the relation between the orbit of a secondary electron generated therefrom and the surface charge.

FIG. 4 is a drawing showing a technique for increasing the quantity of an electron beam by changing the focal point of a first condenser lens in performing pre-dose.

FIG. 5 is a drawing showing a technique for increasing the quantity of an electron beam by changing the diameter of an aperture of a diaphragm on a passage of the electron beam in performing pre-dose.

FIG. 14 is a drawing schematically showing the potential distribution formed by pre-dose and the orbit of the primary electron beam according to the position of incidence.

FIG. 15 is a drawing schematically showing the secondary electron image of a contact hole generated when the contact hole is observed by an electron beam entering a wafer perpendicularly or obliquely.

FIG. 19 is a drawing schematically showing the relation between the total quantity of secondary electrons passing the energy filter and charge of the sample.

FIG. 22 is a drawing schematically showing a sample of a display onto a screen of the database relating the wafer kind and the pattern size with the pre-dose condition.

DETAILED DESCRIPTION OF THE PREFERRED EMBODIMENTS

In the description below, mainly in pre-dose, acceleration voltage is changed to the same with higher secondary electron generation efficiency, and a half band width of an electron beam irradiated interlocking with the area of the preliminary irradiation region is changed. Thus, high charge voltage can be formed on a wafer and the electron beam is irradiated to an entire area of the irradiation region, therefore provision of a method and a device capable of forming the charge effectively becomes possible.

Also, a method and a device is described wherein, preliminary irradiation is performed by different acceleration voltage after formation of charge, leveling of the charge formed on the surface of a wafer is performed, thereby leveling of the electric field in the vicinity of the wafer formed by the charge voltage becomes possible, and the electric field component in the direction perpendicular to the light axis of the electron beam can be decreased. Thus, even if the potential on the surface of the wafer changes with the lapse of time, the electron beam is not subjected to deflection by the electric field component in the lateral direction, therefore occurrence of drift is inhibited.

Furthermore, because the pre-dose technology described below uses an electron optical system used for observation, structural modification such as a flat gun is not required. Therefore, cost increase can be inhibited, and constitution of the device satisfying requirement of users is possible.

Below, the embodiments of the pre-dose technology will be described referring to drawings.

Figure 1:
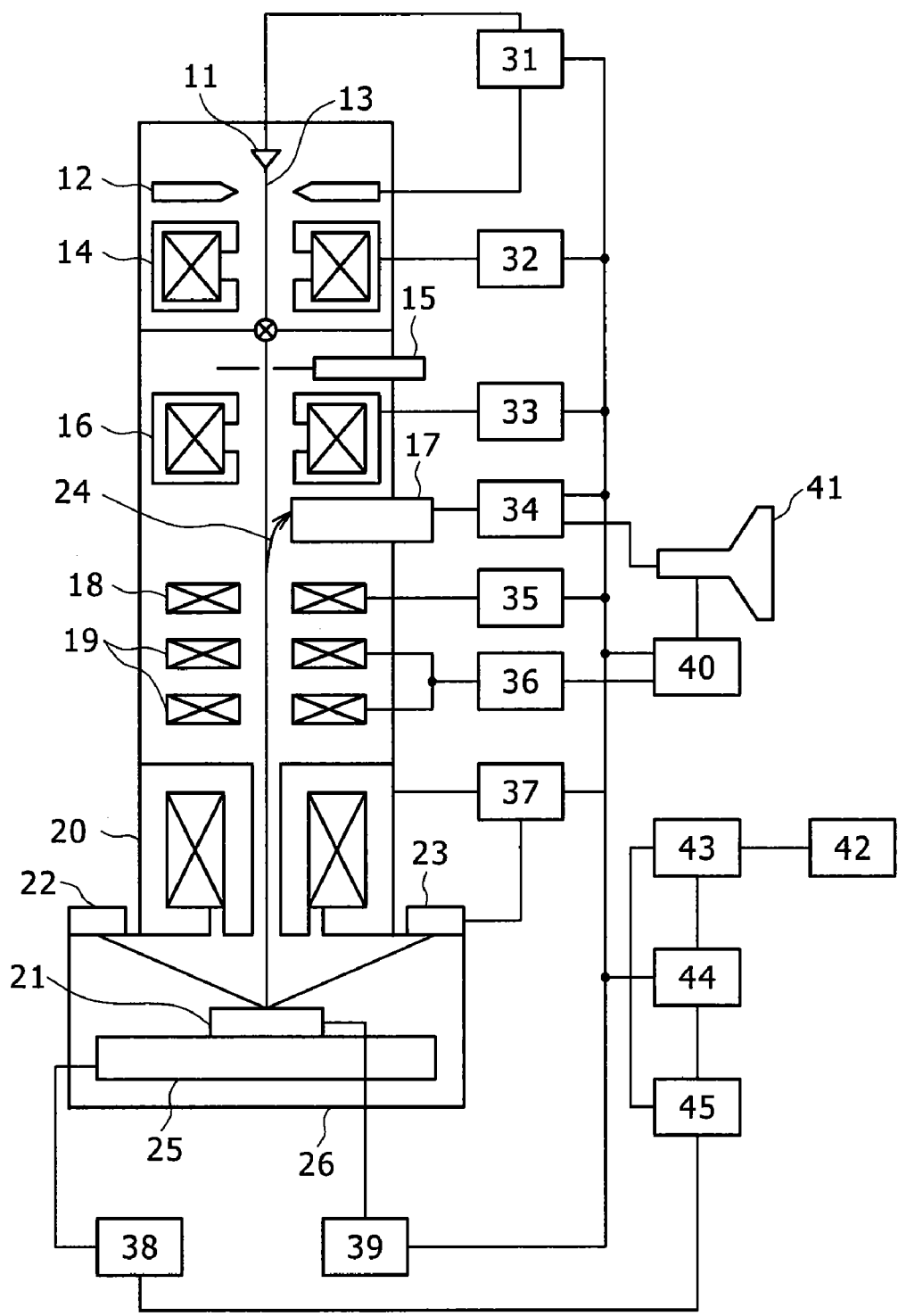
FIG. 1 is a drawing showing the overall configuration of a scanning electron microscope.

FIG. 1 shows the overall configuration of a scanning electron microscope. A whole control unit 43 controls the whole device through an electron optical system control device 44 and a stage control device 45 on the basis of the acceleration voltage of an electron, the information of a wafer 21, the observation position information and the like, input by an operator from a user interface 42.

The wafer 21 is fixed onto a sample stage 25 in a sample chamber 26 through a wafer conveying device not shown after going through a sample exchange chamber.

In accordance with the direction from the whole control unit 43, the electron optical system control device 44 controls a high voltage control device 31, a retarding control unit 39, a first condenser lens control unit 32, a second condenser lens control unit 33, a secondary electron signal amplifier 34, an alignment control unit 35, a deflection signal control unit 40, and an objective lens control unit 37.

A primary electron beam 13 drawn out from an electron source 11 by a draw out electrode 12 is converged by a first condenser lens 14, a second condenser lens 16 and an objective lens 20 and is irradiated onto the wafer 21. On the way, the electron beam is subjected to adjustment of its orbit by an alignment coil 18 and is two-dimensionally scanned on the wafer 21 by a deflection coil 19 which received a signal from the deflection signal control unit through a deflection signal amplifier 36. To the wafer 21, retarding voltage (negative voltage in an electron microscope) is applied from the retarding control unit 39 to slow down the electron beam. Originating irradiation of the primary electron beam 13 to the wafer 21, a secondary electron 24 discharged from the wafer 21 is captured by a secondary electron detector 17 and is used as a brightness signal of a secondary electron image display device 41 through the secondary electron signal amplifier 34. Also, because the deflection signal of the secondary electron image display device 41 and the deflection signal of the deflection coil 19 are synchronized, the pattern shape on the wafer 21 is faithfully reproduced on the secondary electron image display device 41.

Further, a diaphragm 15 is arranged on the irradiation light axis of the primary electron beam 13. This diaphragm 15 has a function of adjusting the quantity of the primary electron beam irradiated to the wafer 21 and has an action of producing a beam open angle to minimize the total quantity of the aberration (diffraction aberration, chromatic aberration, spherical aberration) of the objective lens 20.

The electron optical system control device 44 is constituted to control the negative voltage applied to the sample, the deflection coil (scanning deflector) and the lens according to the established energy reaching the sample, the magnification, the beam diameter and the like of the electron beam. For example, switching of electron beam energy reaching the sample is performed by adjustment of the applied voltage of negative voltage to the sample. Also, switching of energy reaching the sample may be performed by changing the applied voltage to, for example, an accelerating electrode (not shown) or an electrode equivalent to it.

For inspecting and observing the pattern on the wafer 21 at high speed, it is necessary to detect the height of the wafer 21 when the sample stage 25 moves to the desired observation point, and to match the focus of the objective lens according to the height. Therefore, wafer height detecting function using light is provided. The position of the sample stage is detected by a sample stage position detect unit 38, a height detect laser beam emitter 22 irradiate the light toward the wafer 21 since the sample stage 25 nears the vicinity of a predetermined position, its reflection light is received by a position sensor 23, and the height of the wafer 21 is detected based on the light receiving position.

And a focus amount according to the detected height is fed back to the objective lens through the objective lens control unit 37. As a result, when the sample stage 25 reaches a predetermined position, the focus has been already set, and detection of the pattern can be performed automatically without operation by an operator. Further, although description is made below referring to an example of a semiconductor wafer as an observation object by an electron beam, there is no necessity to limit to it and a mask or the like used in transcription of a semiconductor pattern may be its observation object.

The objects of measurement using a scanning electron microscope for semiconductor processes are gate wires, wire width for bit calling of a transistor, and the aperture diameter of the contact hole for securing electrical conductivity between layers. With respect to the contact hole, in particular, as multilayering proceeds accompanying high integration of a semiconductor, the depth of the contact hole is deepened, and the aperture diameter becomes small accompanying micronization.

For example, in some of the 45 nm node semiconductors which currently are under development for commercialization, the depth of the contact hole is 1.5 to 2.0 μm and the aperture diameter is approximately 50 nm. In such a contact hole, the aspect ratio, which represents the ratio of the depth of the hole to the aperture diameter, exceeds 30.

FIG. 2 shows an example of the shape of a contact hole and an orbit of a secondary electron. Generally, the contact hole 52 is provided for connecting between layers of a semiconductor device. Therefore, a substrate 51 is constituted of conducting material such as silicone, an insulation film 50 is formed thereon, and the insulation film 50 is etched to form the contact hole. In the drawing, H represents the depth of a contact hole 52, D represents the diameter of an aperture at the bottom of the contact hole 52, and the aspect ratio of such contact hole 52 is represented by H/D. To measure the aperture diameter D of the contact hole 52, not only the secondary electron from the hole surface but also the secondary electron 24 from the bottom must be detected. However, in a contact hole with a large aspect ratio, the secondary electron 24 generated at the aperture part of the hole, in many cases, collides the side wall of the hole and disappears on the way of travelling upwardly from the hole, and cannot be captured by the secondary electron detector 17. As a result, the shape of the aperture part cannot be constructed as a secondary electron image, therefore the aperture diameter cannot be measured as well.

As a means for solving this problem, a technique called pre-dose to form charge on the wafer 21 is adopted. Pre-dose means a method wherein an electron beam is irradiated to the surface of the wafer 21 in which the contact hole is shaped to produce positive charge 53, and the secondary electron is lifted up to the surface of the wafer 21 by an electric field of the potential difference against the bottom of the contact hole.

In the gazette for the Japanese Published Unexamined Patent Application No. 2000-200579, for example, with respect to the acceleration voltage of a primary electron beam irradiated to produce charge, it is disclosed that the secondary electron generation efficiency (the ratio of generation of the secondary electrons from the wafer 21 to the incident quantity of the primary electron beam to the wafer 21) must be 1 or above. By performing this pre-dose, easy detection of the secondary electrons generated from the bottom of the contact hole 52 became possible, and observation of the shape and measurement of the size have been performed.

However, there are problems also in this pre-dose method. As described above, to form the positive charge on the surface of the wafer 21, it is necessary to irradiate a primary electron beam for a fixed period of time and form the stable charge. Also, to lift up the secondary electron, a definite electric field is required, and this electric field is determined by the surface potential of the wafer 21 and the depth H of the contact hole. When the contact hole is deep, higher positive charge is required compared with the case of a shallow one. As is described also in WO03/007330, the irradiation area of the primary electron beam should be made wide to raise the charge voltage. However, as the irradiation area is made large, the density of the electron within the irradiation region is lowered, therefore the time until the charge is stabilized becomes necessary. As a result, because measurement takes longer time, the throughput is lowered and the cost is increased. Below, an embodiment effective in forming charge on the surface of the wafer 21 efficiently will be described.

Figure 3:
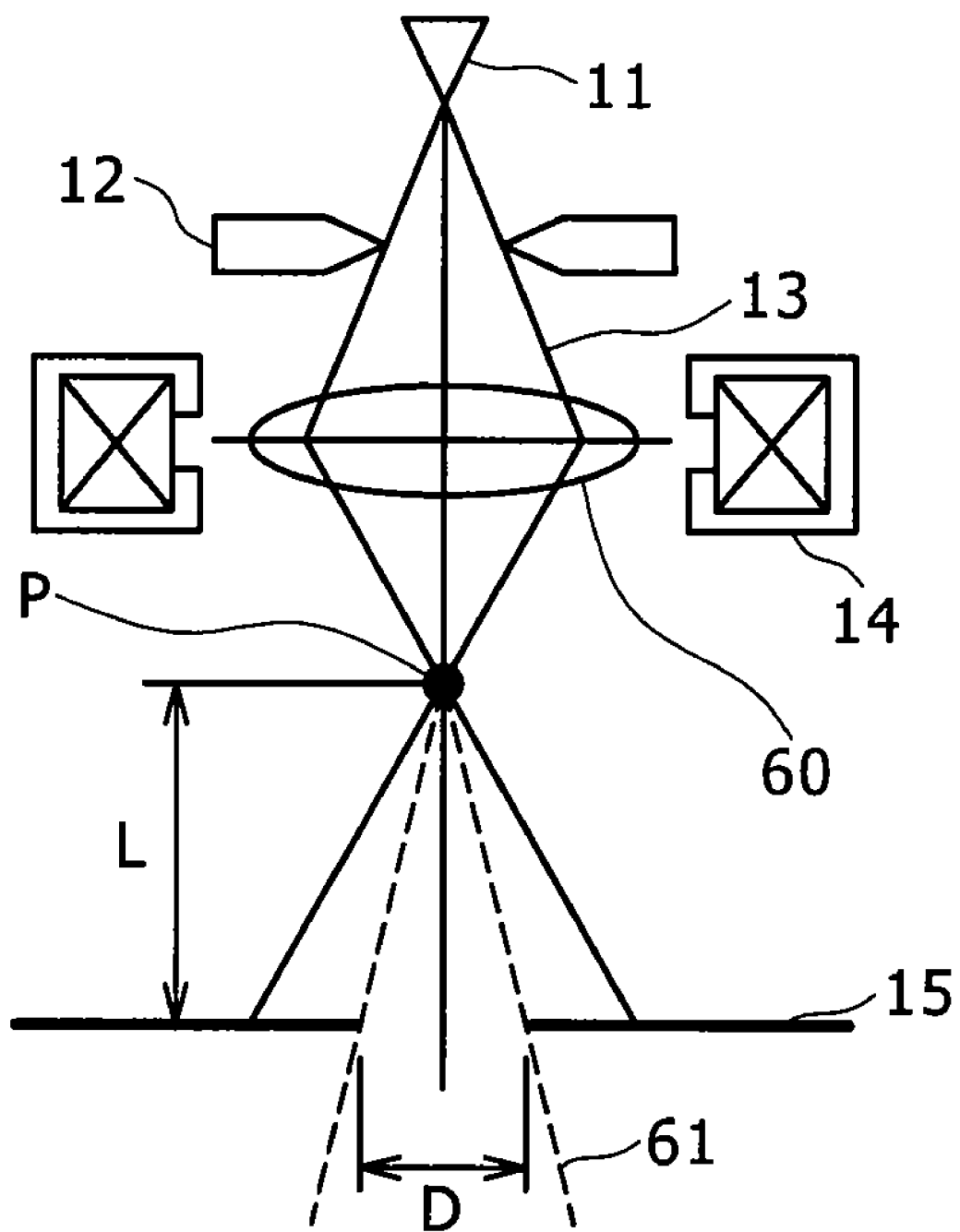
FIG. 3 is a drawing showing the relation between an electron source, a first condenser lens and a diaphragm, and an electron beam.

FIG. 3 shows the relation of the electron emitted from the electron source 11, and the first condenser lens 14 for converging it and the diaphragm 15 disposed on the passage of the electron beam. Onto the diaphragm 15, the electron 13, which is emitted from the electron source 11 and converged at a position apart from the diaphragm 15 by a distance L by a magnetic field 60 formed by exciting the first condenser lens 14, is irradiated. A round-shape aperture with a diameter D is formed in the diaphragm 15, and a portion of the electrons 13 reached to the diaphragm passes this aperture and reaches onto the wafer 21.

The ratio of the electrons 13 which reach the diaphragm 15 to the electrons 61 which are a part thereof and pass the diaphragm 15 is same with the ratio of the solid angle of each of them. Consequently, in performing pre-dose, if the ratio of this solid angle is changed, the quantity of the electrons reaching the wafer 21 can be increased, decrease of the electric charge density by irradiation of electrons to a wide area can be inhibited, and the time required for pre-dose can be shortened. FIG. 4 shows a technique of changing the electron quantity by changing the convergence position of the first condenser lens 14. When L represents the distance between the convergence position of the first condenser lens 14 and the diaphragm, and D represents the diameter of the diaphragm, the approximation equation for the solid angle θ of the electron beam passing the diaphragm can be represented by the equation (1).

$$\theta = (D/L)^2 \quad (1)$$

A current amount passing the diaphragm is proportionate to this solid angle. For example, as shown in FIG. 4, the crossover position in observation and measurement of the shape is P1, the distance to the diaphragm becomes L1, and a little current is used to decrease the damage of the sample. On the other hand, when pre-dose is performed, a large current is required, therefore the crossover position is changed to P2 and the distance to the diaphragm is shortened to L2. If the crossover position P2 is changed to, for example, such a position as satisfying the equation of 2L2=L1, the current amount passing the diaphragm becomes 4 times based on the equation (1). If this relation is applied, the irradiation electron quantity in pre-dose can be changed optionally.

FIG. 5 shows a technique to change the electron quantity by changing the aperture diameter of the diaphragm. In the diaphragm 15, a plurality of apertures with the different diameter are provided. The aperture used for measurement is with a smaller diameter of D1 for letting a little electric current passes, and the aperture used in pre-dose is with a larger diameter of D2 for letting a large electric current passes. The ratio of the electron quantity when these different apertures are used follows the equation (1), and, for example, when 2D1=D2, the electron quantity becomes 4 times.

Figure 6:
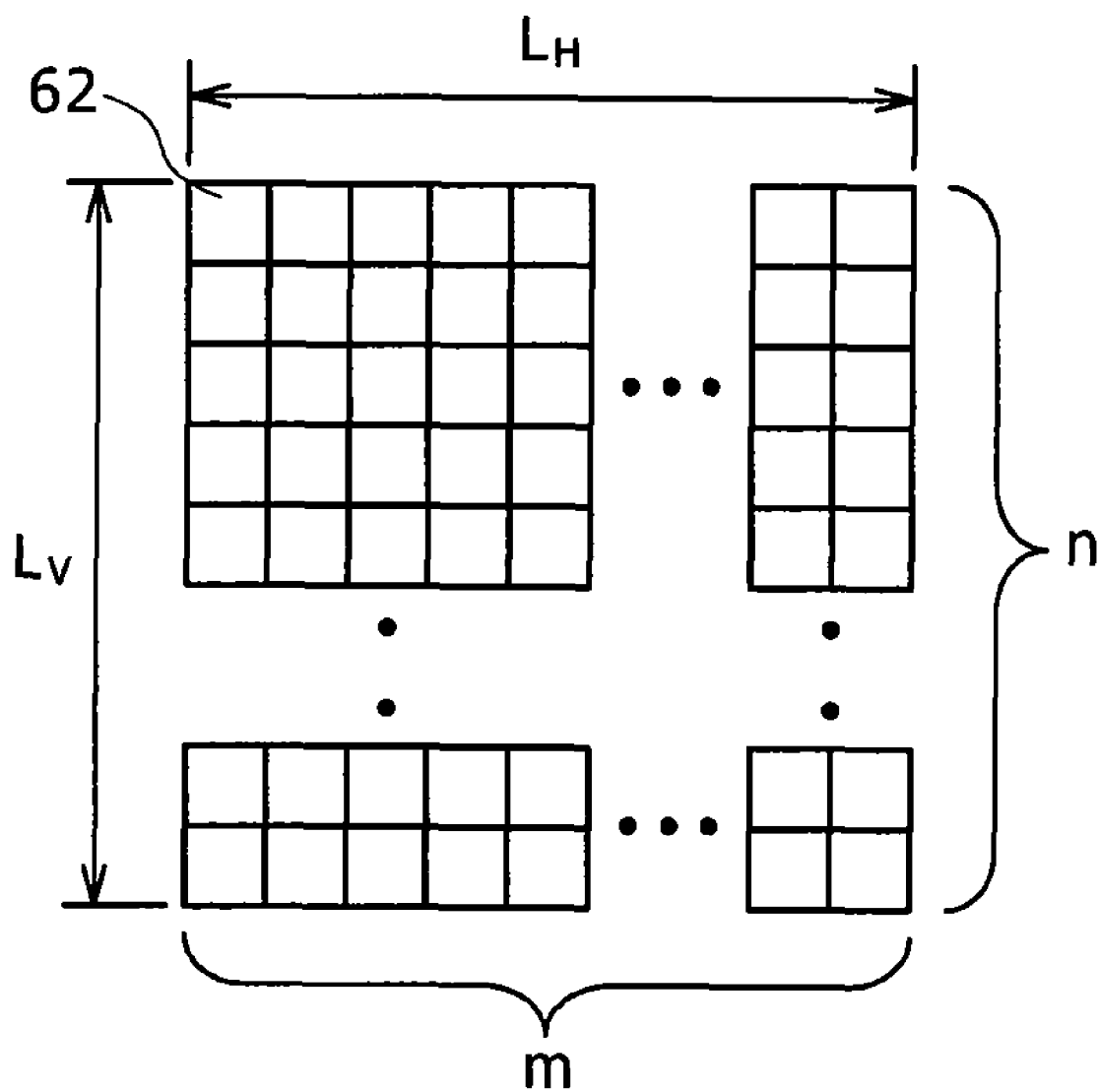
FIG. 6 is a drawing showing the relation between the irradiation region of an electron beam on a wafer and the pixel of a device indicating a secondary electron image.

So far, a method to form charge efficiently by increasing the electron quantity in pre-dose has been described. Apart from it, by the relation between the scanning interval of the electron on the wafer 21 and the half band width of the electron converged by the objective lens also, the time required for charging and the charge voltage differ as well. FIG. 6 shows the irradiation region on the wafer 21 and the scanning interval of the electron beam. LH and LV in the drawing represent the length of the irradiation area 62 of the primary electron on the wafer 21, and are determined by the magnitude of the display region of the secondary electron image display device 41 and the observation magnification in displaying on the display device. For example, when the display region of the image on the image display device 41 is 135 mm×135 mm and the observation magnification is 1,000 times, LH and LV become the same length which is 135 mm÷1,000=0.135 mm. Further, the display device has pixels of a finite number, and the shape of the pixels generally is square whose numbers m and n become equal.

Figure 7:
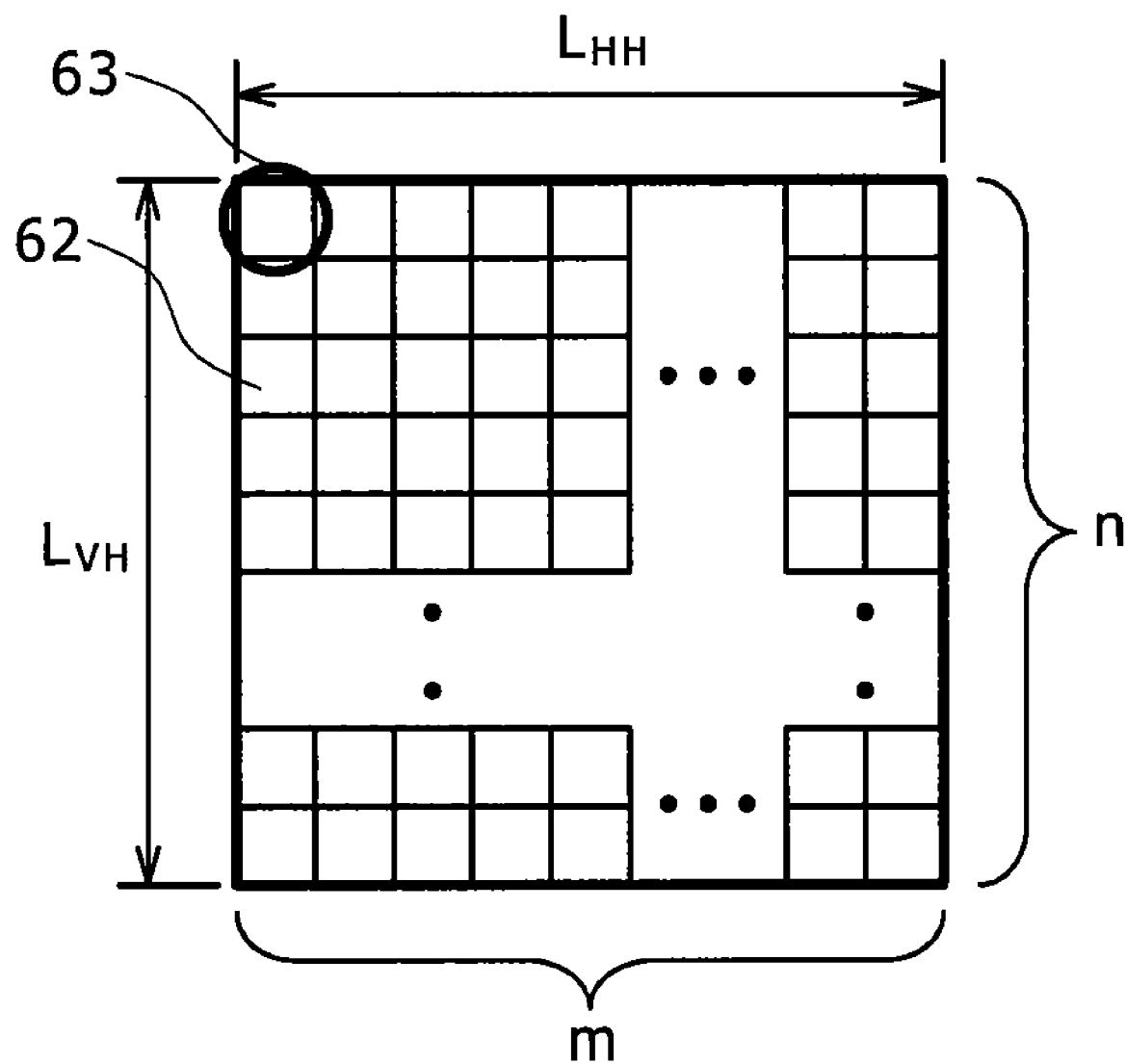
FIG. 7 is a drawing showing the relation between the scanning interval of a primary electron beam in a high observation magnification and the half band width of a primary electron beam.

When the number of the pixel is 512, the interval of the scanning lines on the wafer 21 can be calculated by the scanning area on the wafer 21 and the pixel number, and becomes 0.135 mm÷512 pixels≈264 nm. FIG. 7 shows the relation between the scanning interval on the wafer 21 and the half band width of the electron beam in observation by a high magnification. The resolution of electron beam devices used for semiconductor processes is approximately 2 nm at present. Even at a low acceleration voltage (for example, the secondary electron generation efficiency is said to be highest when the acceleration voltage is approximately 300 V to 400 V in a silicon dioxide-based insulation film used for semiconductor) with high secondary electron generation efficiency (ratio of the generated quantity of the secondary electrons to the quantity entering the wafer 21 of the primary electron beam) used for pre-dose, the resolution is approximately 4 nm. When observed by a high magnification of, for example, 200,000 times, the scanning interval of the electron beam on the wafer 21 becomes 1.32 nm from the relation described above.

Figure 8:
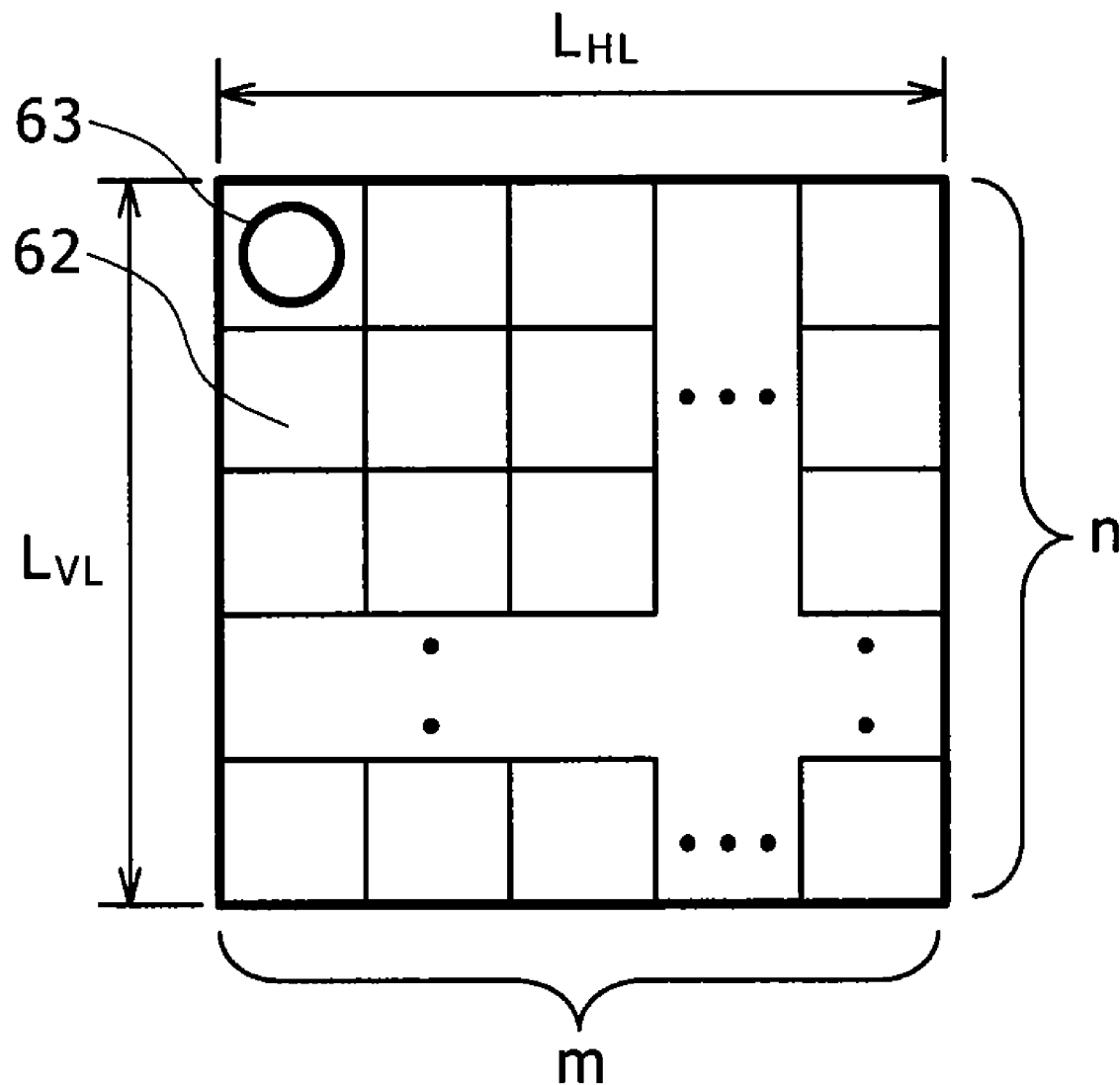
FIG. 8 is a drawing showing a scanning interval of a primary electron beam in such a low observation magnification as in the case pre-dose is performed and a half band width of the primary electron beam.

Consequently, in such observation by a high magnification, as shown in FIG. 7, because the scanning interval is smaller than the half band width 63 of the electron beam, the electron beam is irradiated to the entire scanning area on the wafer 21. However, as shown in FIG. 8, in the scanning area used in performing pre-dose, the scanning interval of the electron beam, which is, for example, approximately 264 nm in the condition of 1,000 times described above, is much larger than the half band width 63 of the electron beam, which is 4 nm, for example, therefore if such electron beam with small half band width is used, the electron beam is not irradiated to major part of the irradiation region. In such a case, because of the effect of the region where the electron beam is not irradiated, charge formed on the surface of the wafer 21 becomes low in average.

Figure 9:
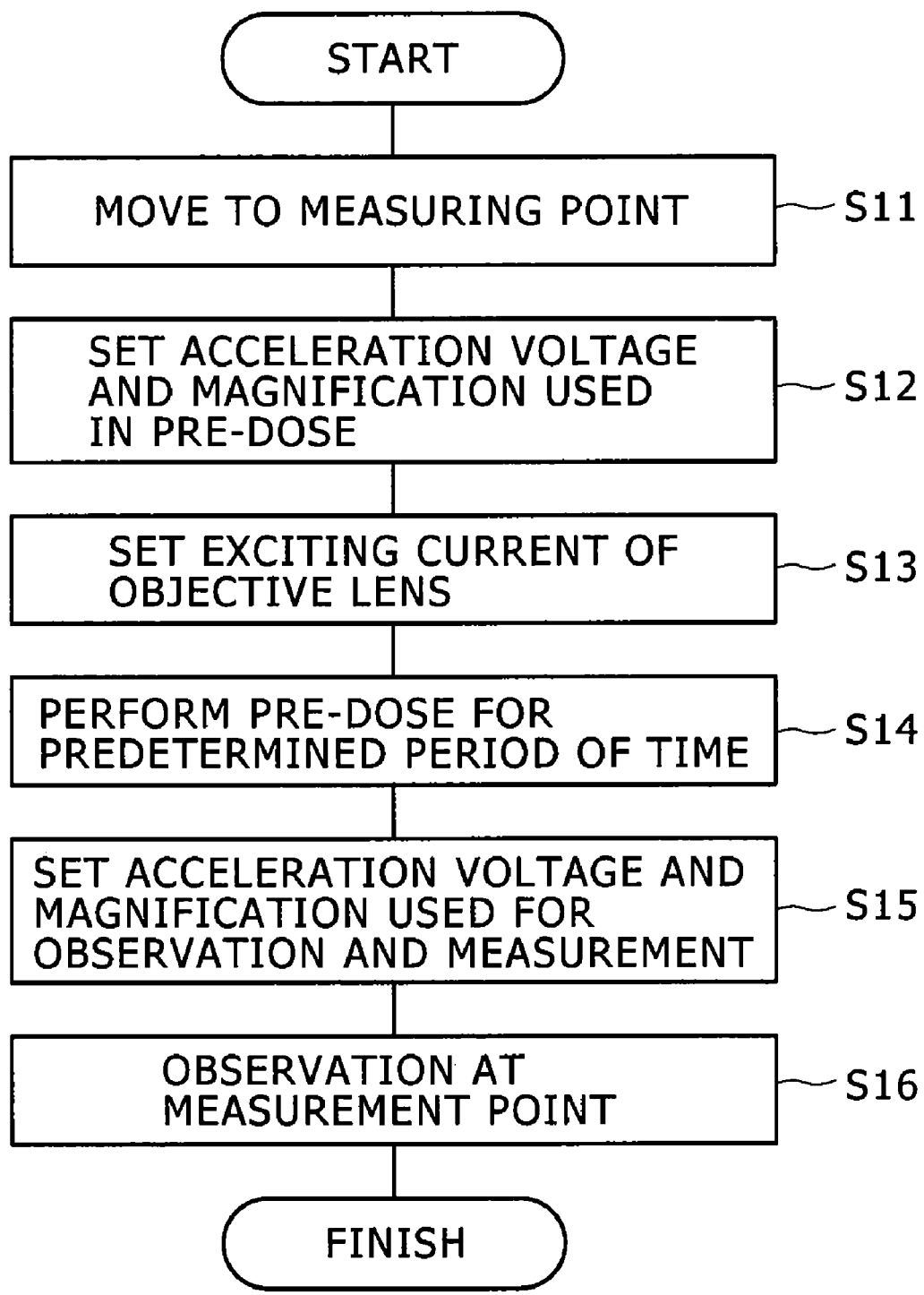
FIG. 9 is a drawing showing a process flow of the case pre-dose is performed using an electron beam whose half band width is made larger than the scanning interval by changing the focus of an objective lens.

Accordingly, it is possible that the charge required for observation of the contact hole with high aspect ratio cannot be formed. To solve such a problem, pre-dose is carried out in accordance with the procedures shown in FIG. 9. First, move to a measuring point where observation by a high magnification is performed (S11). Thereafter, the magnification and the acceleration voltage are set to the execution condition of pre-dose (S12), then, the exciting current of the objective lens is set to either stronger exciting side or weaker exciting side than the exciting current intrinsically required for convergence on the wafer 21 by the acceleration voltage for pre-dose (S13). After setting, pre-dose is performed (S14).

After pre-dose is finished, the condition of the electron optical system is set to the magnification, acceleration voltage, and exciting current used for observation (S15), and observation by a high magnification is executed (S16). With respect to the condition of the exciting current in S13, it is important that the half band width of the electron beam on the wafer 21 is set to at least larger than the scanning interval. Also, in this example, a half band width is used for exemplary description as an indicator representing the beam diameter, but it is not necessary to limit to it, and if there is a more appropriate parameter for representing the magnitude of the beam diameter, such a parameter may be defined for the beam diameter. In pursuing the aim of leveling the unevenness of the potential distribution within the electron beam scanning region in pre-dose, if there is a more suitable parameter, it is desirable to select it.

Figure 10:
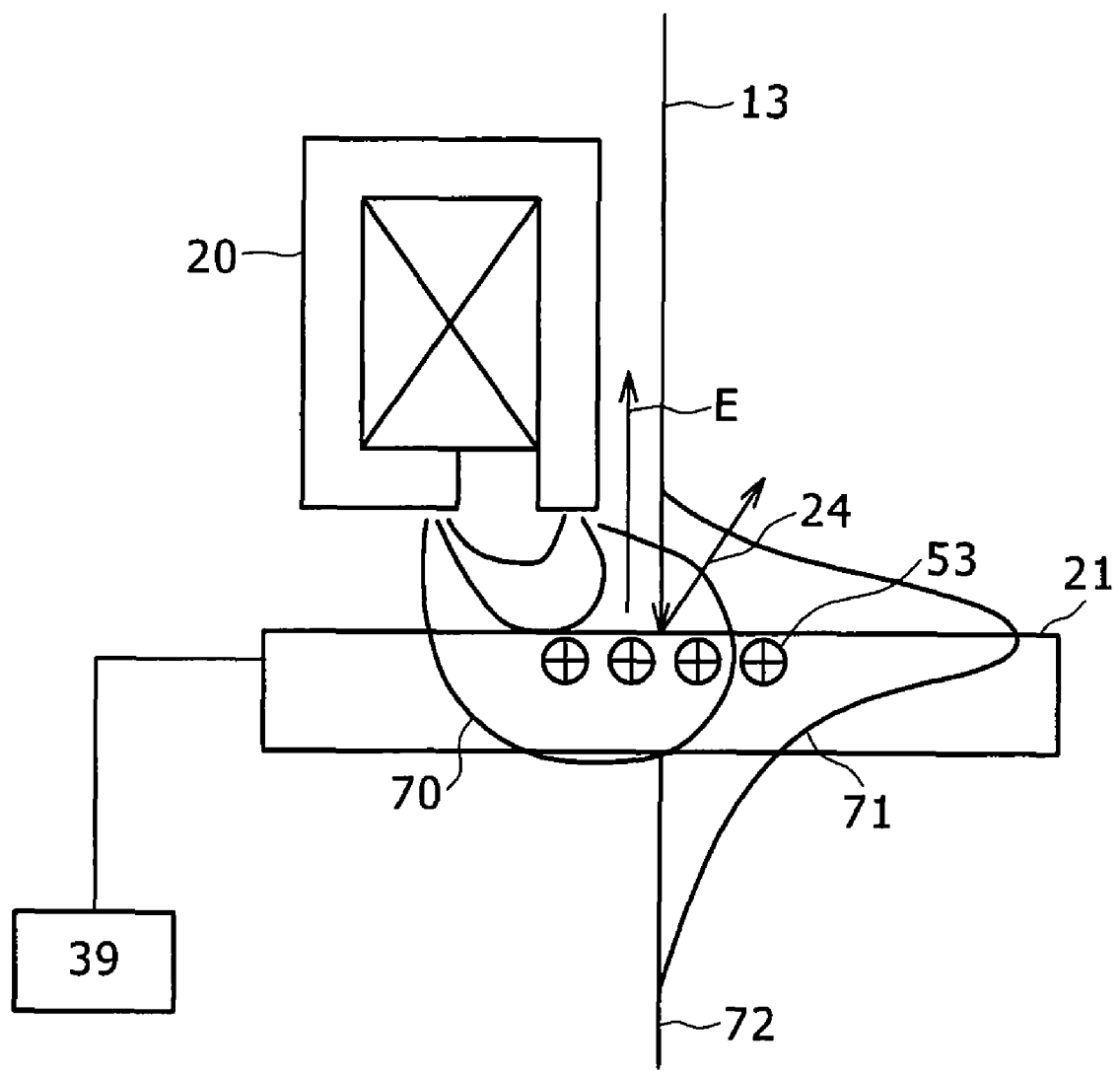
FIG. 10 is a drawing schematically showing the relation between the magnetic field of an objective lens and the potential distribution in the vicinity of a wafer applying to a secondary electron generated from the wafer.

First, a scanning interval is calculated in accordance with a control program in the electron optical system control device 44 based on the acceleration voltage and the magnitude of the irradiation region in pre-dose. Based on the calculated scanning interval, the exciting current of the objective lens for realizing the electron beam having a large half band width larger than at least the scanning interval is calculated in accordance with the exciting current control program. Also, it is desirable that the electron beam diameter required is realized by setting the exciting current to the stronger exciting side. The reason will be described referring to FIG. 10. On the wafer 21, a magnetic field 70 of the objective lens 20 is leaked out and a magnetic field distribution 71 is formed on a light axis 72 of the electron beam. Further, to the secondary electron 24 generated by irradiation of the electron beam 13, a force F shown in the equation (2) is applied.

$$F = e(v \times B) + e \cdot E \tag{2}$$

where: e represents energy of the secondary electron. The first term of the equation (2) represents the force by the magnetic field 70 applied to the secondary electron, v is the kinetic vector of the secondary electron 24, and B is the vector representing the direction of the magnetic field of the objective lens.

Also, the second term of the equation (2) represents a force by the electric field applied to the second electron, and E is the vector representing the line of electric force in the vicinity of the wafer 21 determined by the voltage applied to the wafer 21 by the retarding control unit 39 and the potential of the objective lens, or the charge voltage of the wafer 21 accompanying generation of the secondary electron 24.

When the positive charge is formed in the wafer 21, the force to draw back the secondary electron to the wafer 21 becomes strong according to the second term of the equation (2) resulting in neutralization of the formed charge, and the charge voltage lowers. Under such situation, if the magnetic field 70 is strengthened, the first term of the equation (2) becomes large which results in hindering the secondary electron generated from the wafer 21 from returning to the wafer 21, and large positive charge can be formed on the wafer 21. This is the reason why it is desirable to set the exciting current in pre-dose to the stronger excitation side and to enlarge the electron beam diameter.

On the other hand, forming of excessive charge in the wafer 21 leads to increase the risk of electrostatic breakage at the boundary face of the contact hole, therefore forming appropriate charge is important. Even though the charge voltage of the wafer 21 lowers because of the reason described above if the weaker exciting side is used, there is also an advantage of lowering the risk of electrostatic breakage. Accordingly, the electron beam diameter may be enlarged in the weaker exciting side.

Figure 11:
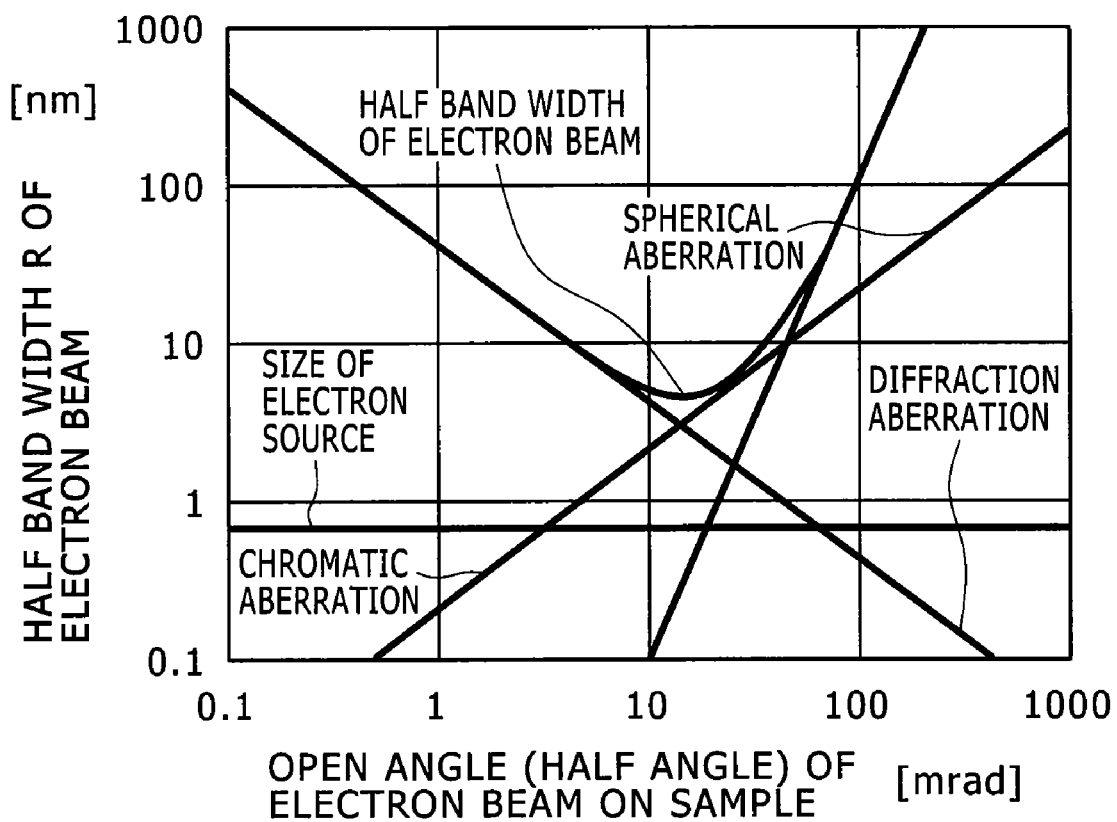
FIG. 11 is a drawing showing the relation of the open angle of an electron beam irradiated onto a wafer, the aberration of an objective lens, and the half band width of the electron beam calculated therefrom.

FIG. 11 shows a method using aberration of the objective lens for enlarging the half band width of the electron beam. The half band width R of the electron beam can be represented by the equation (3).

$$R = (0.61 \times \lambda/\alpha)^2 + ((1/2) \times (\Delta E/E) \times C_c \times \alpha)^2 + ((1/4) \times C_s \times \alpha^3)^2 + (R_{ss} \times M)^2 \tag{3}$$

Here, the first term represents a blur due to diffraction of an electron, λ represents the wavelength of the electron beam, and α represents the open angle (half angle) of the electron beam on the wafer 21. The second term represents a blur due to the chromatic aberration, ΔE represents the expanse of energy the electron beam has, E represents the acceleration voltage of the electron beam in pre-dose, $C_c$ represents the chromatic aberration coefficient of the objective lens. The third term represents a blur due to the spherical aberration, and $C_s$ represents the spherical aberration coefficient of the objective lens. The fourth term represents reflection of the magnitude of the electron source onto the wafer 21, $R_{ss}$ represents the magnitude of the electron source, and M represents the magnification of the electron optical system. The graph shown in FIG. 11 shows the relation of the open angle, various aberrations and half band width of the electron beam. As will be understood from the graph, if the open angle is decreased and diffraction aberration is enlarged, or if the open angle is enlarged and spherical aberration is enlarged, the half band width of the electron beam can be enlarged. In the case of using diffraction aberration out of them, the open angle for attaining the half band width of 264 nm becomes approximately 0.14 mrad.

This open angle is, if an open angle in usual observation with high resolution is provisionally assumed to be approximately 14 mrad, approximately 1/100 of it, and it is obvious that the beam current cannot be secured. If this open angle is to be achieved by an electron optical system, the aperture diameter of the diaphragm 15 is to be exemplarily made 1/100 of the usual aperture diameter (0.2 µm against the usual aperture diameter of 20 µm, for example), however, considering how the aperture of this dimension is prepared with high accuracy or possible contamination of the aperture part by irradiation of an electron beam, it is obvious that stable operation as an apparatus for industrial use is difficult.

Accordingly, the method of enlarging the half band width of an electron beam by enlarging the spherical aberration of an objective lens is considered to be appropriate. For example, in a scanning electron microscope with the spherical aberration coefficient of 0.4 mm, to achieve the half band width of 264 nm by spherical aberration, the open angle may made approximately 138 mrad in accordance with the equation (3). If the method shown in FIG. 4, for example, is to be applied, this means the distance between the first condenser lens and the diaphragm in observation is to be made 1/10 which is technically possible.

Also, if the method shown in FIG. 5 is to be applied, the aperture diameter of the diaphragm may be made 10 times, therefore this method is technically possible as well. Further, it is obvious that, by jointly applying this method of enlarging the half band width of an electron beam by enlarging spherical aberration with the method shown in FIG. 4 or FIG. 5, increase of the half band width and increase of the beam current can be realized simultaneously.

Moreover, according to the aspect ratio of the contact hole, required charge quantity differs. Because excessive charging increases the risk of dielectric breakdown of the insulation film 50, it is important to charge appropriately. Although the relation between the irradiation area of pre-dose and the charge voltage is described in WO03/007330, the charge voltage can be controlled by adjusting the time for pre-dose. Therefore, it is also important to adjust the time for pre-dose shown in S14 in FIG. 9 according to the aspect ratio of the contact hole shaped on the wafer 21 observed.

Also, so far, the case of inhibiting non-irradiated region of a beam by enlarging the beam diameter in pre-dose has been described, however, because enlarging the beam diameter means decrease of the irradiation amount per unit area, it is preferable to jointly use the method to increase the electron quantity as described above to supplement it. For example, when the magnitude of the beam diameter is controlled to equate with the distance between scanning lines to fill the space between the scanning lines, the magnitude of the beam diameter changes according to the magnification. Consequently, by controlling so that the beam current increases as the magnification decreases (as the scanning region is widened), above supplement becomes possible. Furthermore, the absolute quantity of the beam fed in is adjustable by control of the number of frames (the number of times of scanning of two-dimensional region), therefore the beam current may be controlled instead of or jointly with controlling of beam current amount.

So far, a method for increasing the electron beam quantity in pre-dose and a method to increase the half band width of the electron beam considering the scanning interval on the wafer 21 in pre-dose for efficiently performing pre-dose have been described. Although, pre-dose itself is a very important technology for charging, the primary purpose is to perform stable observation or reproducible measurement of dimensions of the bottom of a deep contact hole. To attain the purpose, stable scanning of the primary electron beam on the wafer 21 in observation performed after pre-dose is important.

Figure 12:
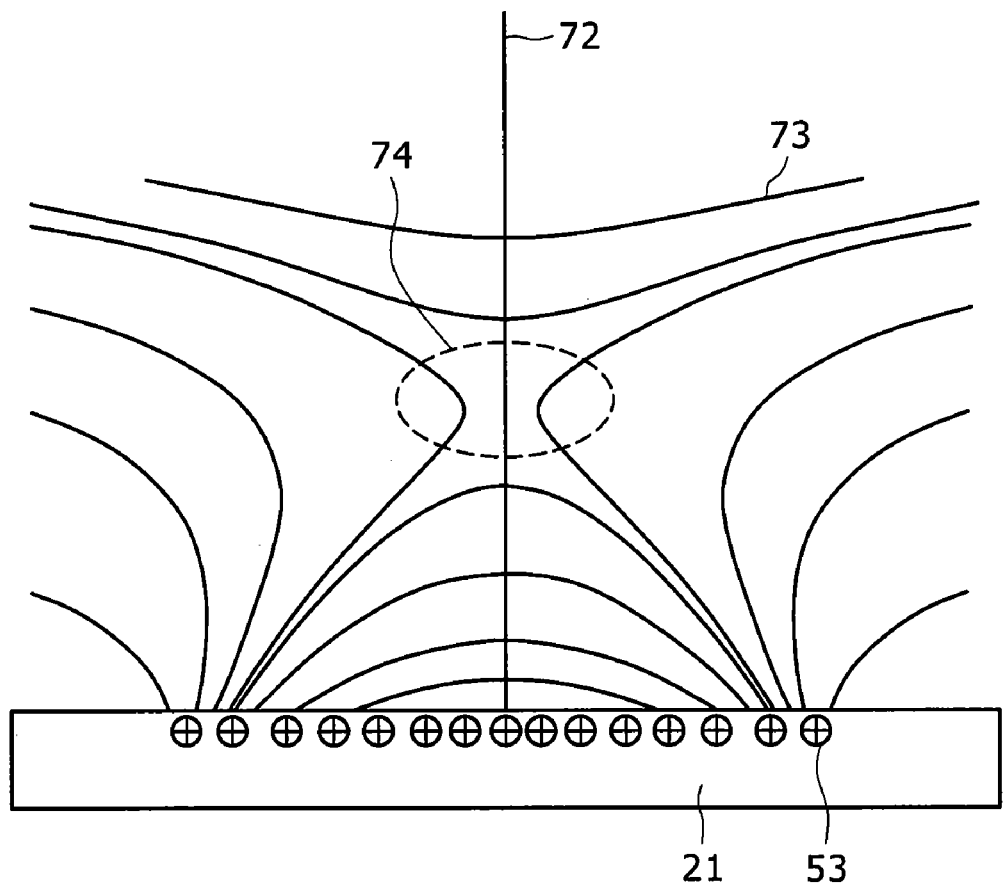
FIG. 12 is a drawing schematically showing the potential distribution in the vicinity of a wafer generated by the charge formed on the surface of the wafer by pre-dose.

FIG. 12 schematically shows the potential distribution generated by the charge formed on the surface of the wafer 21 by pre-dose. The charge on the surface of the wafer 21 starts to be formed soon after start of irradiation of the primary electron beam 13 and the charge voltage gradually increases. As the charge voltage increases, an equipotential line 73 shown in FIG. 12 extends to the irradiation region and forms a potential black point 74.

The equipotential line 73 extended and the potential black point 74 become a potential barrier for the secondary electron generated from the wafer 21 and act as the force to prevent the secondary electron from traveling upward and to draw it back to the wafer 21. Also, this barrier does not work evenly over the entire irradiation region but works conspicuously toward the peripheral part within the irradiation region. These phenomena occur continuously within the irradiation region, and after some time, irradiation of the primary electron 13 and generation of the secondary electron 24 are balanced resulting in formation of the charge having distribution on the wafer 21. Further, this potential distribution varies according to, for example, scanning of the electron beam in observation and movement of a charge within the wafer 21.

In particular, when the primary electron beam 13 is scanned on the wafer 21 for observation, symmetry of charge varies according to its acceleration voltage and scanning direction. If the symmetry is lost, the potential distribution having the component perpendicular to the traveling direction of the electron beam and varying with respect to time is formed. As a result, a time change of the reaching position of the electron beam onto the wafer 21, that is, a drift phenomenon of the electron beam, occurs which becomes the cause of a blur of an image in observing by a high magnification. To solve this problem, it is important that the potential distribution generated by pre-dose has not steep variation, and stabilization of charge voltage by stepwise pre-dose under a plurality of conditions as measures for its realization will be described hereinbelow.

Figure 13A:
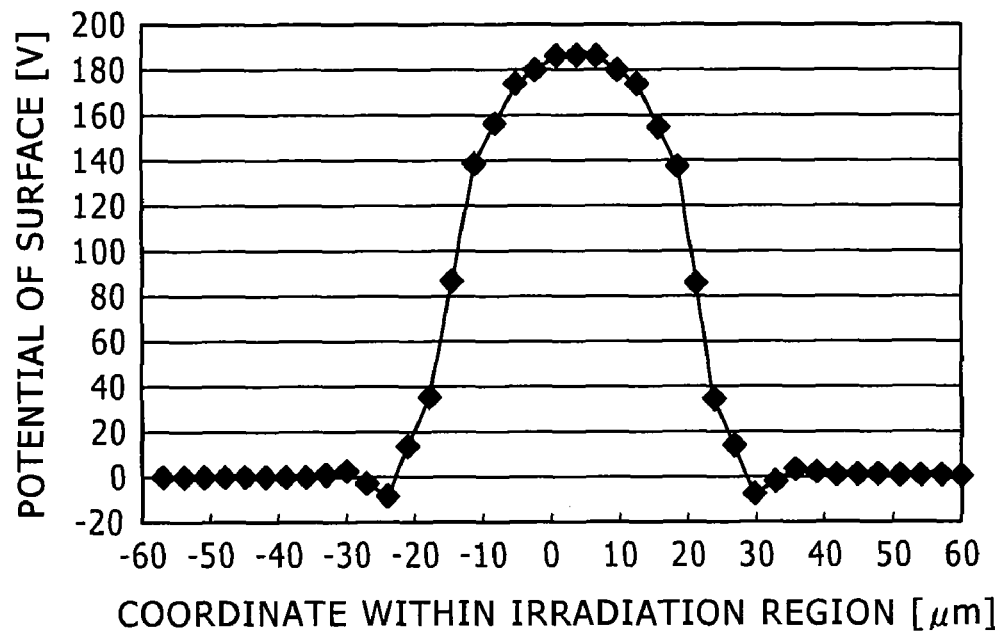
FIG. 13 is a drawing showing the result of a simulation by a computer on the potential distribution formed on the surface of a wafer by pre-dose and the potential distribution when the second stage pre-dose is performed.
Figure 13B:
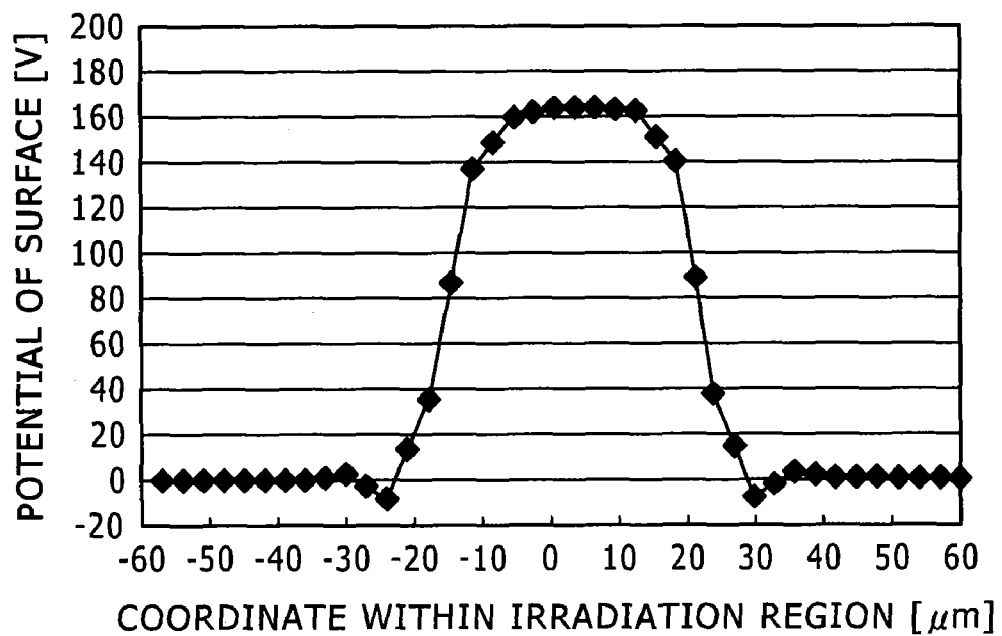

FIG. 13 is the result of the calculation by computer simulation of the potential distribution generated by pre-dose, and both (a) and (b) show the potential distribution on the center line of the irradiation region. (a) of FIG. 13 is a result of the simulation of the charge potential generated by pre-dose of the first step when 120 µm square on the oxide film (silicon dioxide) is made the irradiation region with 300 V acceleration voltage and 80 pA primary electron beam 21 quantity in pre-dose.

The result shows that the charge potential is highest as approximately 180 V in the center of the irradiation region, and has such potential distribution as, the farther from the center of the irradiation region, the lower the charge potential. (b) of FIG. 13 shows the result of the simulation of the charge potential after the pre-dose of the second step is performed for the irradiation region of 60 µm square with 1,600 V acceleration voltage and 8 pA primary electron beam 21 quantity after the charge potential shown (a) is formed.

It can be seen that the potential distribution of a wide region including the observation point is flattened by pre-dose of the second step. The causes of it are that, because the acceleration voltage in pre-dose of the second step is 1,600 V, the generation efficiency of the secondary electron is inhibited compared to that in 300 V, and that, because a portion of the secondary electrons generated from the pre-dose region of the second step is attached again to the 60 µm square and its outer region, the density of the positive charge within the pre-dose region of the second step lowers thereby the potential lowers as well.

As described above, by dividingly performing pre-dose in at least 2 steps, the potential distribution of the observation region at least can be made uniform or near to uniform state, and inhibiting the drift phenomenon of the electron beam becomes possible. Its principle will be described hereinbelow in more detail.

First, the electron beam with 300 eV energy reaching a sample is irradiated to a non-charged sample and the surface of the sample (the electron beam with high secondary electron generation efficiency) is charged (pre-dose of the first step). Because the secondary electron generation efficiency in the electron beam of 300 eV is 2.0 under a certain condition, it becomes such a state that 2nos of electrons are emitted from the sample against 1no of electron is fed in, and 1no of positive hole is generated in the sample against 1no of electron is fed in. This in turn forms the positive charge.

Further, this positive charge forms a potential barrier on the sample as described previously. As the potential barrier gradually becomes larger by accumulation of charges, the electrons that cannot go beyond the potential barrier increase responding to it. Thereafter 1no of electron is fed in, 2nos of electrons are emitted from the sample against it, then, under the state that 1no of electron is returned to the sample side by the potential barrier, and the state of charge becomes stable.

Next, the pre-dose of the second step is performed by scanning the electron beam of the reaching energy with low secondary electron generation efficiency compared with that of the pre-dose of the first step. In this example, the pre-dose of the second step is performed using the electron beam of 1,600 eV reaching energy. The secondary electron generation efficiency of the electron beam of 1,600 eV is made 1.2. In other words, when 1no of electron is fed in, 1.2no of electron is emitted from the sample on the calculation.

With respect to the electron emitted here, 0.6no of electron returns to the sample by the potential barrier previously formed. By this, 0.4no of electron is accumulated in the sample, the charge potential lowers, and the potential barrier becomes slightly small. It becomes the same state that 1no of electron is fed in and 1.2no of electron is emitted from the sample. At this time, because the potential barrier is less than the initial state, the number of the electrons returning the sample decreases also (0.35no, for example). If this state further continues, for example, under the state 1no of electron is fed in and 1.2no of electron is emitted, it becomes the state that 0.2no of electron returns to the sample by the potential barrier. That means the numbers of the electrons fed in and the electrons emitted become equal and the charge becomes stabilized state.

As described above, by performing the pre-dose of the second step so that the peak of the potential distribution formed by the pre-dose of the first step is flattened, inhibiting of the drift phenomenon and the like in beam scanning for observation thereafter becomes possible.

In this aspect, the pre-dose of the first step for forming large charge is performed first, and to shape the potential distribution formed by the pre-dose of the first step, the pre-dose of the second step is performed. The condition for this time is the relation of $\delta_1 > \delta_2 > 1.0$ between the secondary electron generation efficiency $\delta_1$ of the electron beam used for the pre-dose of the first step and the secondary electron generation efficiency $\delta_2$ of the electron beam used for the pre-dose of the second step. In the state wherein $\delta_2$ is less than 1.0 (that is, the state wherein the electrons fed in is more than the electrons emitted), negative charge continues to increase simply and the charge is not stabilized.

In the pre-dose of the first step, an electron beam having the secondary electron generation efficiency that is necessary for that the charge quantity increases first and is stabilized after some time by the effect of the potential barrier formed thereby and the like is used, whereas in the pre-dose of the second step, an electron beam having the secondary electron generation efficiency that is necessary for that the charge quantity decreases first and is stabilized after some time by the effect of the potential barrier formed in the first step and the like is used.

In this aspect, the reaching energy of an electron beam satisfying the conditions described above is set.

Although it was stated as above that reduction of the gradient of the potential produced by pre-dose is important for reducing drift of the electron beam, it is obvious that the charge region formed by pre-dose must include the observation and measurement point. Also, it is preferable that the center of the irradiation region where pre-dose is performed coincides with the point where observation and measurement are performed. One reason is to reduce the drift described above and another is for perpendicular incidence of the primary electron beam to the wafer 21.

FIG. 14 exhibits the problem occurring when the center of the primary electron irradiated for observation is shifted from the center of the charge region formed by pre-dose. If the primary electron beam 13 is made incident to the center of the charge region, it is irradiated perpendicularly to the wafer 21, but if it is made incident from a point other than the center, it is made incident to the wafer 21 obliquely by refracting action by an electric field formed by the charge. When the contact hole 52 is observed using the primary electron beam made incident perpendicularly, the upper opening and the bottom opening are observed in the position symmetric to the contact hole 52 as shown in FIG. 15, however, when observed by the primary electron beam 13 made incident obliquely, the bottom opening of the contact hole 52 is shifted from the center according to the incident direction.

Figure 16A:
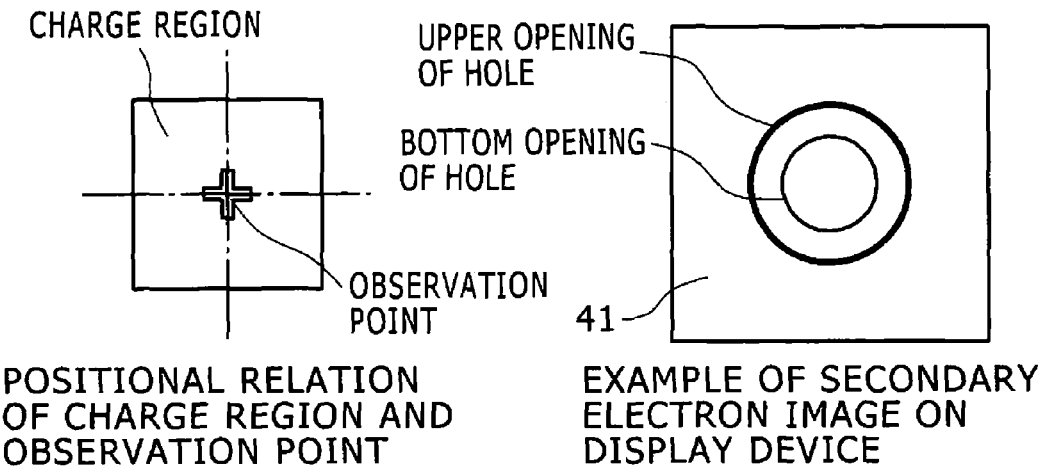
FIG. 16 is a drawing schematically showing the position relation between the charge region formed by pre-dose and the observation region, and looks of a secondary electron image obtained thereby.
Figure 16B:
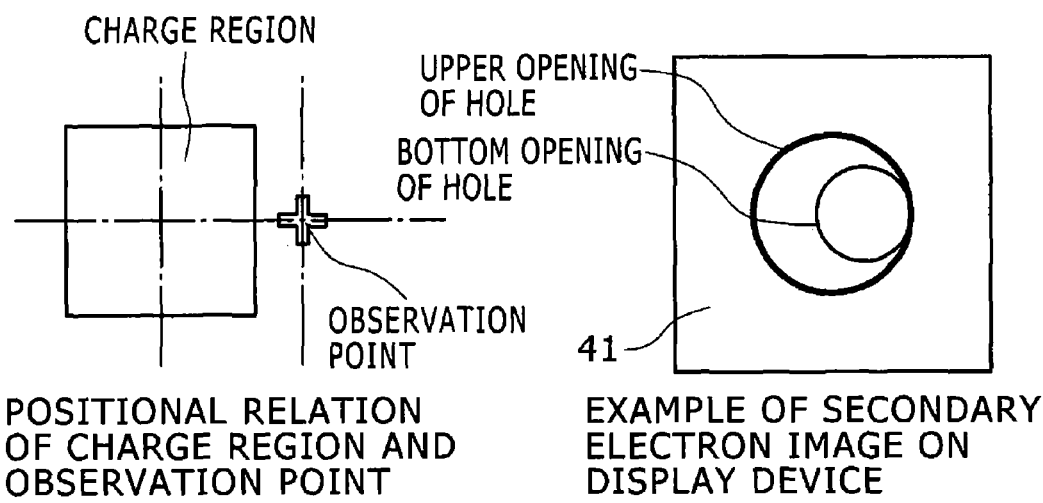

If oblique incidence is extreme with the incident angle larger than the angle of the side wall of the contact hole 52, for example, observation of the edge of the bottom in the incident direction becomes impossible and accurate shape cannot be captured. Accordingly, in performing pre-dose, alignment for centering the position for observation is important using, for example, an alignment coil 18 shown in FIG. 1 and the like On the other hand, by intentionally shifting the point for observation of the contact hole and the like and the center of the charge region formed by pre-dose, the primary electron beam can be made oblique. As described above, when pre-dose is performed using the acceleration voltage wherein the secondary electron generation efficiency exceeds 1, positive charge is formed on the surface of the sample. On the other hand, the primary electron beam has negative charge. Therefore, the primary electron beam is inclined by a deflecting action to the direction where positive charge exists. The inclination angle of the primary electron beam is proportionate to the charge voltage and the distance between the charge region and the observation point. FIG. 16 is an example schematically showing the relation of the position of observation and the charge region and inclination direction, and the secondary electron image on the display device.

In FIG. 16 (1), the center of the contact hole for observation and the center of the charge region formed by pre-dose coincide, and there is no deflecting action the primary electron beam receives from the charge region in observation in this case. Therefore, the contact hole is observed symmetrically.

On the other hand, FIG. 16 (2) shows an example wherein the charge region is to the left of the center of the observation point. In this case, the primary electron beam in observation is subjected to deflecting action of the positive charge formed in the charge region and curves to the left, and is made incident obliquely to the wafer. As a result, observation of the left inner wall of the contact hole becomes possible. Although FIG. 16 shows the case wherein the charge region and the observation point are in entirely different position relation, the observation point may be included within the charge region.

This inclined observation method does not require new construction for inclination, and is effective as a technique for easy observation of the side wall of a contact hole and a line pattern. Further, because deflecting action to the primary electron beam applies in the position where the electron beam has been almost converged, geometric aberration for inclination and off-axis chromatic aberration generated by that the beam passes off the axis of the objective lens are less. Consequently, an inclined image of high resolution can be obtained.

According to one of the aspects described above, even for the contact hole with high aspect ratio formed on the wafer by micronization of a semiconductor, observation and measurement become possible without performing pre-dose for a long period of time.

The technique described above can be used as one of the automatic measuring functions normally used in a scanning electron microscope for a semiconductor. Furthermore, the techniques described in the present invention, with the exception of the part that electric current of pre-dose is changed by enlarging the aperture diameter of the diaphragm, can be realized by changing the control program only with the hardware structure of the existing scanning electron microscope remaining unchanged, and adjustment of an electron optical system and the like accompanying the modification of the hardware is not required. The user can enjoy great merits related with introduction such as saving the purchase cost of functions and shortening the downtime of the device.

As described above, for observation, inspection or measurement of a contact hole with high aspect ratio, it is necessary to form charge on a sample by irradiation of an electron beam, however, on the other hand, forming of excessive charge may cause great damage to a semiconductor formed on a wafer. For example, if the thickness of the insulation film 50 shown in FIG. 2 is assumed to be 1.5 μm, and the charge voltage after pre-dose is assumed to be 160 V from the result of FIG. 13(*b*), a very strong electric field of approximately $1.07 \times 10^8$ (V/m) is formed between the surface of the contact hole and the substrate 51.

In the experiments by the present inventors, discharge was not confirmed under the condition described above, however, if voltage resisting performance of the insulation film 50 is lower than the above figure, the positive charge accumulated on the surface of the insulation film is discharged toward the substrate 51, and damage is caused to the insulation film and the substrate by energy of discharge at that time.

However, the condition under which the discharge phenomenon occurs depends on the kind, thickness, insulation performance, and surface charge of the insulation film. Therefore, the irradiation condition of pre-dose must be determined while confirming possibility of observation of the bottom of the contact hole by performing pre-dose for an actual device while preventing occurrence of the discharge phenomenon by formation of excessive charge. At the same time, it is also important to keep the pre-dose condition and the charge voltage at that time and the-like as quantitative data and lower the risk of occurrence of the discharge phenomenon in a new device which will be made thereafter.

With this regard, performing pre-dose while measuring charge voltage is proposed as a technique to quantify the condition wherein observation of the bottom of the contact hole is possible, and its device constitution and technique will be described hereinbelow.

Figure 17:
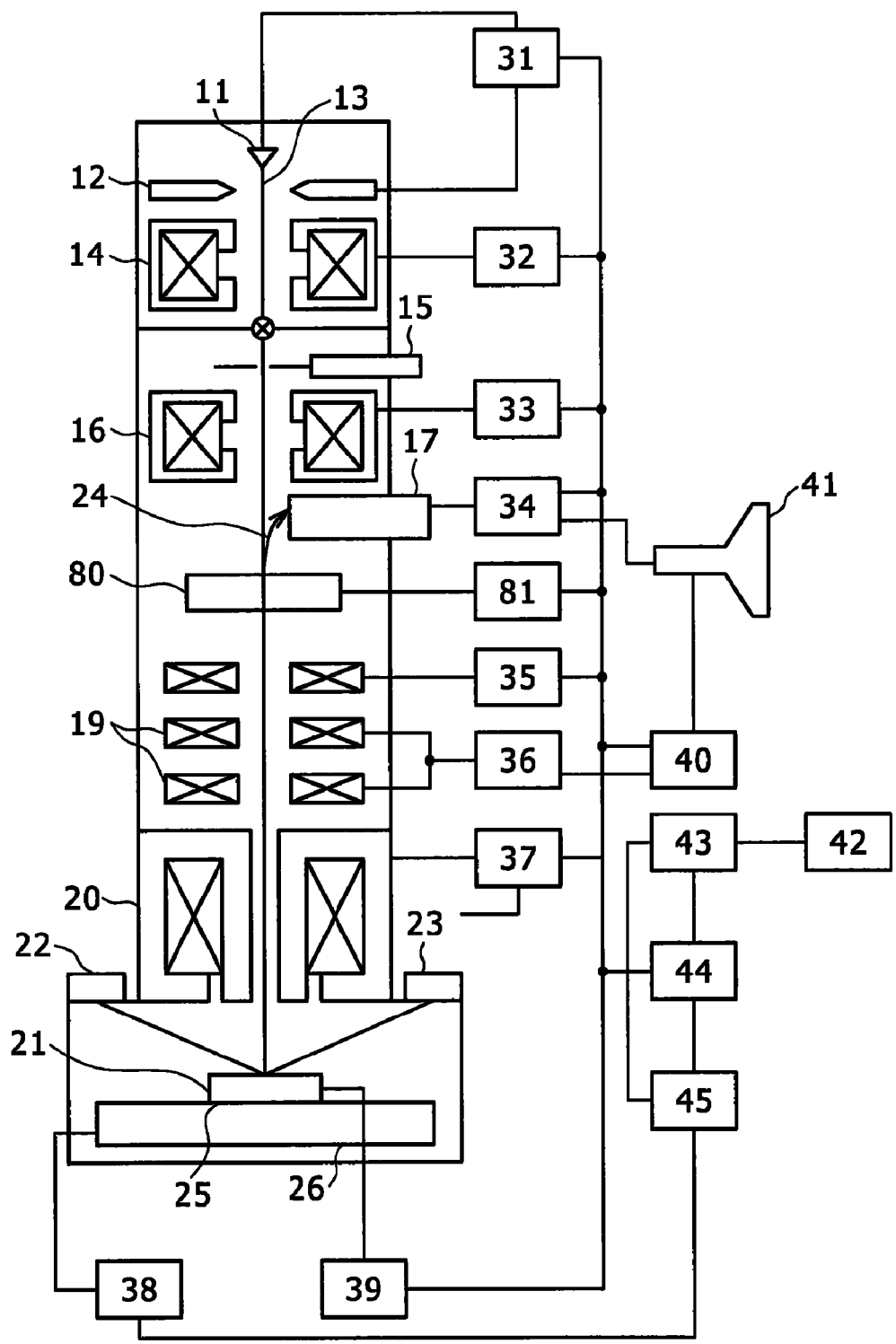
FIG. 17 is a drawing showing the overall configuration of a scanning electron microscope equipped with an energy filter for measuring charge.

FIG. 17 shows a device constitution provided with an energy filter in an electron optical system as one technique for measuring charge voltage.

An energy filter 80 is a device disposed between the second electron detector 17 and the wafer 21 to measure the surface charge of the wafer 21 by measuring energy of the secondary electron generated from the wafer 21. To the energy filter 80, negative voltage is applied in measuring energy through an energy filter control unit 81.

A measuring method of charge voltage by the energy filter 80 will be described briefly referring to FIG. 18. In measuring energy of the secondary electron 24, negative voltage $V_f$ is applied to the energy filter 80 through the control unit 81. The secondary electron 24 is generated from the sample with a variety of initial energy $V_p$ according to the difference in the physical generation process. Thereafter, it is accelerated by retarding voltage $V_r$ applied to the wafer 21, therefore, immediately before the energy filter, energy $V_e$ of the secondary electron 24 becomes $V_p + V_r$. Further, when the charge voltage $V_s$ by pre-dose is formed on the surface of the wafer 21, the energy $V_e$ of the secondary electron 24 becomes $V_p + V_r - V_s$. Here, $V_p$ and $V_r$ are negative potential and $V_s$ is positive potential.

Figure 18A:
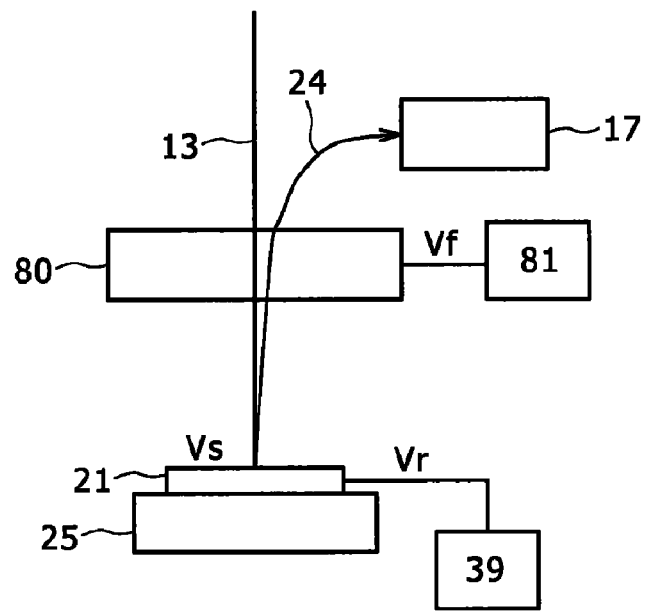
FIG. 18 is a drawing schematically showing the difference of the orbit according to the voltage of an energy filter and energy of a secondary electron.
Figure 18B:
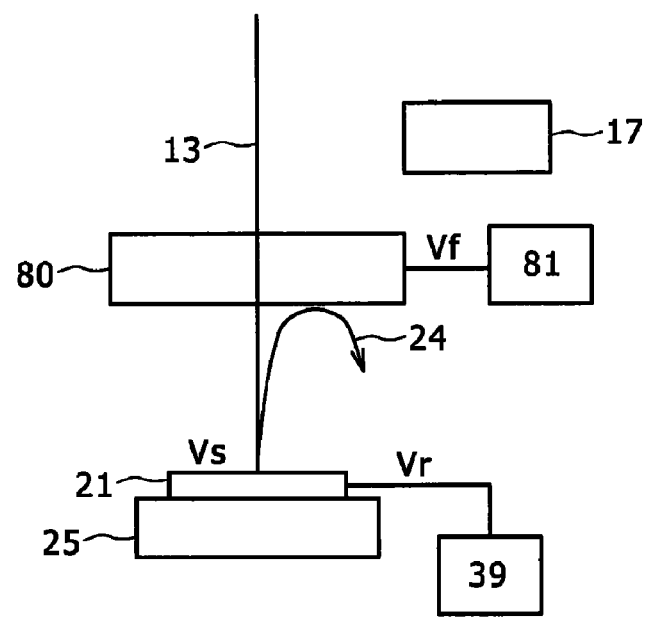

When the magnitude relationship of $V_f$ and $V_e$ is $|V_f| \leq |V_e|$, the secondary electron 24 can pass through the energy filter because its energy is higher than that of the energy filter 80 and can be detected by the secondary electron detector 17 (FIG. 18(*a*)). However, when the voltage of the energy filter becomes high as $|V_f| > |V_e|$, because the secondary electron 24 cannot pass through the energy filter, it cannot be detected by the secondary electron detector 17 (FIG. 18(*b*)).

Based on this relation, if the secondary electron 24 which has passed through the energy filter 80 is detected by the secondary electron detector 17 while changing the applied voltage $V_f$ of the energy filter 80, S-shaped output curves of the secondary electron detector as shown in FIG. 19 are obtained. In FIG. 19, the curves obtained when the retarding voltage $V_r$ applied to the wafer 21 is −2,500 V and the charge voltage is 0 V and 100 V are exemplarily shown.

When the charge potential $V_s$ is 0 V, that is, when the sample is not charged, such output curve (a) as that quantity of the secondary electrons 24 passing through the energy filter and detectable by the secondary electron detector 17 decreases from where the voltage $V_f$ exceeds −2,500 V is obtained, and when the charge potential $V_s$ is 100 V, such output curve (b) as that quantity of the secondary electrons 24 passing through the energy filter and detectable by the secondary electron detector 17 decreases from where the voltage $V_f$ exceeds −2,400 V is obtained. By catching $V_f$ where the detected quantity of the secondary electrons 24 decreases, the charge voltage of the sample can be measured.

Figure 20A:
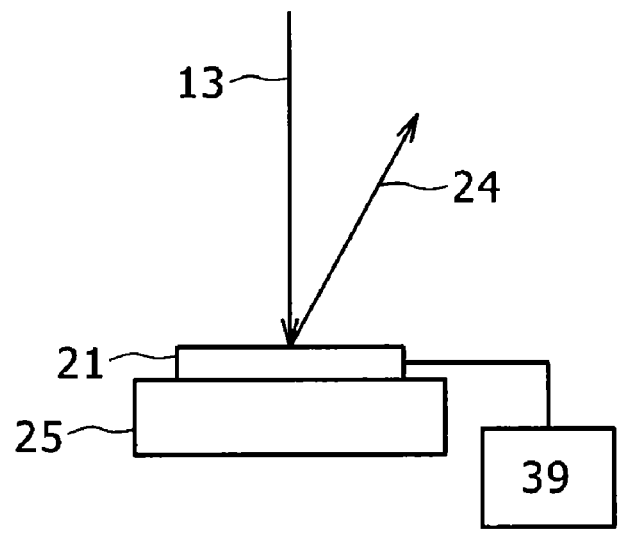
FIG. 20 is a drawing schematically showing the difference of the orbit of a primary electron beam according to a magnitude relation of energy of a primary electron beam and the potential on the surface of a wafer.
Figure 20B:
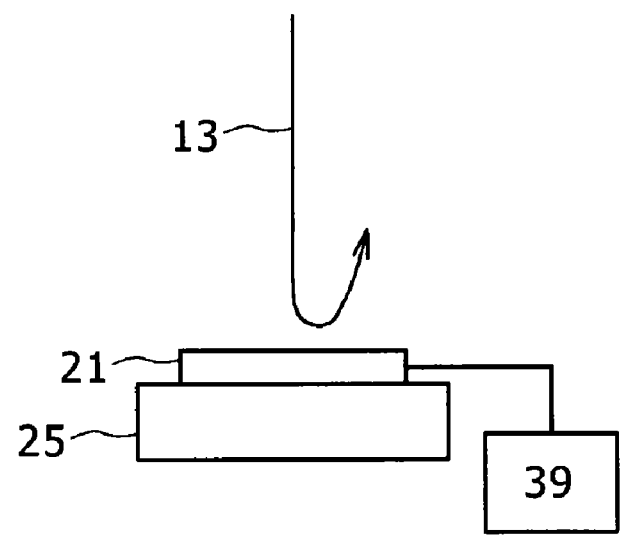

FIG. 20 shows a method which utilizes reflection of the primary electron beam 13 in the vicinity of the sample as another technique for measuring charge voltage.

The primary electron beam 13 travels within the electron optical system with energy V0, is slowed down by the wafer 21 retarding voltage $V_r$ to become the desired voltage $V_{acc}=V0-V_r$, and is irradiated onto the sample. Both of V0 and $V_r$ are negative voltage, and when observation is performed as an electron microscope, the relation of their absolute values usually is as $|V0|>|V_r|$, therefore, the primary electron beam can reach the wafer 21.

For example, when the surface of the wafer 21 is charged to the voltage $V_s$ by irradiation of the electron beam 13, the potential of the sample viewed from the primary electron beam becomes $V_r+V_s$. When the retarding voltage $V_r$ applied to the wafer 21 is −2,500 V and the charge voltage $V_s$ of the sample is 100 V for example, it becomes −2,400 V. Even in this case, if V0 is larger than −2,400 V in the negative side, the primary electron beam can reach the sample.

However, when the retarding voltage $V_r$ applied to the wafer 21 is made high and the relation with the acceleration voltage V0 of the primary electron beam 13 becomes $|V0|<|V_r+V_s|$, the primary electron beam 13 cannot reach the sample but is reflected above the wafer 21 toward the direction of the charged particle source 11 not shown.

Figure 21:
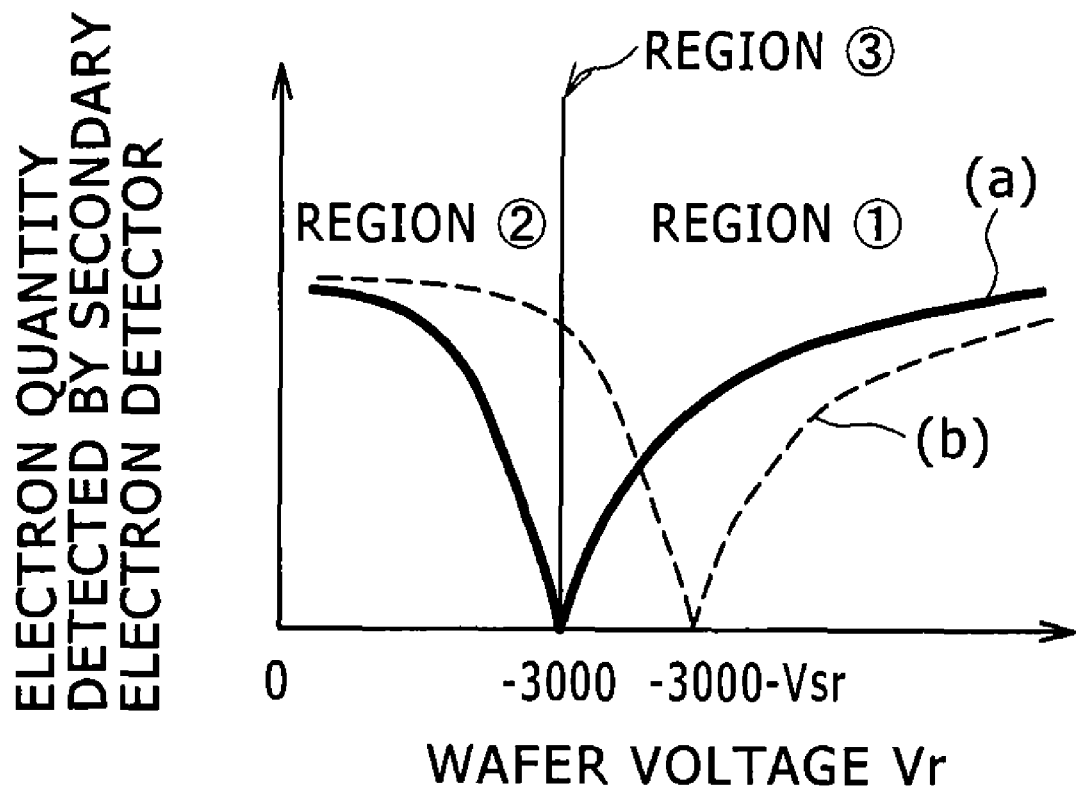
FIG. 21 is a drawing schematically showing the difference of the orbit of a primary electron beam according to a magnitude relation of the charge on the surface of a wafer, with respect to the wafer voltage and the electron quantity detected by a secondary electron detector.

As a result of measuring the electron quantity detected by the secondary electron detector 17 when the retarding voltage $V_r$ is changed utilizing this principle, the output curve shown in FIG. 21 is obtained. The horizontal axis of the graph represents the retarding voltage $V_r$, and the vertical axis represents the quantity of the signal of the electrons detected by the secondary electron detector. Further, the acceleration voltage V0 of the primary electron beam at this time is 3,000 V.

Explanation will be given using the case of FIG. 21(a). (a) represents the case wherein the surface charge $V_s$ of the wafer 21 is 0 V, that is, the case it is not charged. The region [1] shows the area of the condition where the primary electron beam is reflected without reaching the sample because the potential of the sample is higher than the energy of the primary electron beam. At this time, what is detected by the secondary electron detector 17 not shown is not the secondary electron 24 but is the primary electron beam 13.

The region [2] is the region where the primary electron beam 13 can reach the wafer 21 because the energy of the primary electron beam 13 is higher than the potential of the wafer 21 and can generate the secondary electron 24. What is detected by the secondary electron detector 17 is the secondary electron 24 generated at the wafer 21.

The region [3] is the point where the potential of the sample and the energy of the primary electron beam are equal and the primary electron beam is slowed down to 0 V to reach the sample. The primary electron beam 13 can neither reflect nor generate the secondary electron. Consequently, the signal detection quantity at the secondary electron detector 17 becomes zero.

FIG. 21(b) shows the relation between the retarding voltage $V_r$ and the quantity detected by the secondary electron detector 17 when the surface charge voltage $V_s$ of the wafer 21 is $V_{sr}$. By $V_{sr}$, the potential of the surface of the wafer 21 changes from $V_r$ to $V_r+V_{sr}$. Therefore, the region [3] shifts by $V_{sr}$ compared with (a).

Using this principle, the retarding voltage wherein the detection quantity becomes zero is detected by the secondary electron detector 17 while the retarding voltage is changed. If the retarding voltage of that time is $V_{rs}$ and the charge voltage of the sample is $V_{sr}$, the charge voltage $V_{sr}$ can be measured by the relation of $V0=V_{rs}+V_{sr}$.

By using the charge measuring method described above, the charge formed on the surface of the wafer by pre-dose can be measured. With respect to charge measuring techniques, the method using the energy filter and the method utilizing reflection of a primary electron beam were exhibited here, however, it is not necessary to limit to them. For example, a technique is also possible wherein the charge quantity is calculated from variation of focus current before and after pre-dose of the objective lens required for making the primary electron beam 13 converge on the wafer.

Furthermore, by accumulating experiences on optimal pre-dose condition for a variety of patterns and making them database, setting of an optimum condition becomes possible even without measuring charge voltage every time. FIG. 22 shows an example of the database which is displayed on the device by operation on the user interface 42.

The database includes information related to the wafer such as the name of the process in manufacturing a semiconductor, the kind and thickness of the insulation film, dimensions of the contact hole formed, and the conditions of the pre-dose of the first and second steps for it, as well as the charge voltage amount formed on the wafer 21 by those pre-dose conditions.

By displaying this database on a device in setting the measuring condition using the device, it becomes possible to find the condition equal or near to that of the wafer kind on which the measuring condition is to be set and to incorporate it into the sequence of automatic measurement.

Also, in this database, confirmation, addition and deletion of the pre-dose condition responding to the kind of the device are possible. For example, when entirely new type of wafer is measured, its condition can be added to this database. On the other hand, the information of the process already not in use for production may be deleted according to necessity.

Figure 23:
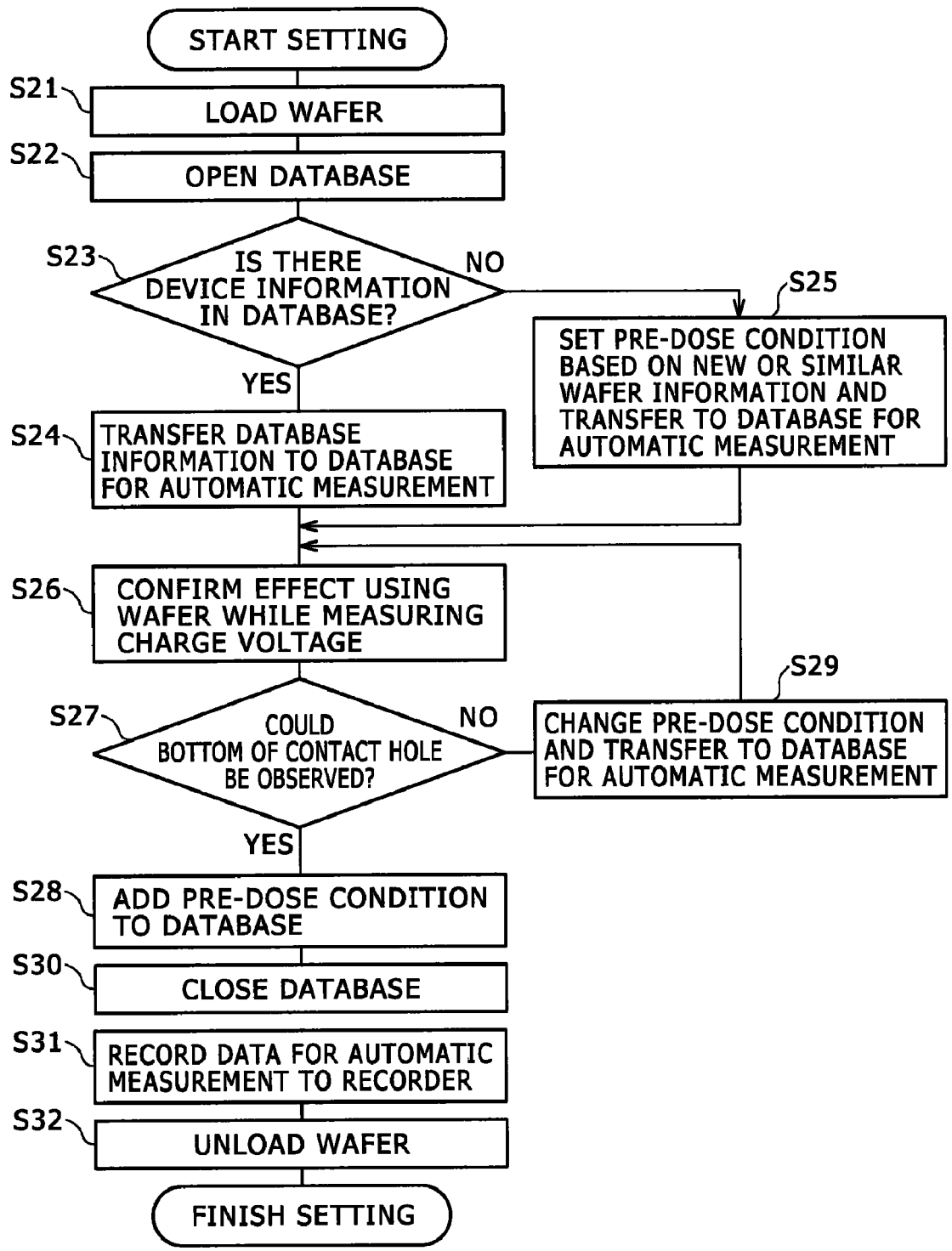
FIG. 23 is a drawing showing a process flow for setting an optimal pre-dose condition referring to the database and actually determining whether the pre-dose condition is good or not using a wafer.

A setting procedure of a pre-dose condition using the database and the measurement technique of the charge voltage described above is shown in FIG. 23. First, the wafer to be measured is loaded onto the device (S21). The database is opened through the user interface (S22), and whether the pre-dose condition corresponding to the wafer to be measured already exists or not is confirmed (S23). If there exists, the pre-dose condition written in the database can be transferred to the file for automatic measurement (S24), and if not, the condition of a similar wafer or the condition based on a past result is written in the file for automatic measurement (S25).

As the first condition setting has been finished, the effect is confirmed using the set pre-dose condition in an actual wafer and the charge voltage is measured (S26). Whether observation of the bottom of the contact hole according to the set condition was possible or not is confirmed (S27), and if yes, its device name, pre-dose condition and charge voltage are added to the database (S28). If not, the pre-dose condition written in the data for automatic measurement is changed (S29), and the effect is confirmed again by observation of the wafer. If the pre-dose condition can be eventually established, the device name, pre-dose condition and charge voltage are added to the database (S28).

Thereafter, the database is closed (S30), the data for automatic measurement with the appropriate pre-dose condition having been written is recorded in a recorder not shown (S31), the wafer used is unloaded from the device (S32), and setting is finished.

Thereafter, in inspecting and measuring the wafer on which the condition is decided according to the procedure described above, if this file for automatic measurement is used, excellent observation can be performed without searching for the pre-dose conditions. Further, as it has been confirmed already that the damage by discharge would not occur, the risk on the production of the wafer can be avoided.

According to one of the aspects described above, performing of observation and measurement of the contact hole with high aspect ratio formed on the wafer accompanying micronization of a semiconductor becomes possible without performing pre-dose for a long period of time.

The technique described above can be used as one of the automatic measuring functions normally used in a scanning electron microscope for a semiconductor. Furthermore, the techniques described in the present invention, with the exception of the part that electric current of pre-dose is changed by enlarging the aperture diameter of the diaphragm, can be realized by changing the control program only with the hardware structure of the existing scanning electron microscope remaining unchanged, and adjustment of an electron optical system and the like accompanying the modification of the hardware is not required. The user can enjoy great merits related with introduction such as saving the purchase cost of functions, shortening the downtime of the device, and reducing the risk of the damage to which the wafer is subjected.

Below, another example of monitoring the charge condition during pre-dose will be described. As described previously, it is desirable to accurately set the charge quantity attached by pre-dose. In this example, a method for accurately controlling the charge quantity by monitoring the charge attached by pre-dose in real time will be described.

When positive charge is attached to a sample by pre-dose, the electron emitted from the scanning region is drawn by the positive charge, therefore it is slowed down by that amount. If the initial acceleration voltage ($V_{acc}$) of the electron emitted from an electron source is 3,000 eV and the retarding voltage ($V_r$) applied to the sample is −2,000 V, the second electron emitted almost without energy (that is, 0 eV) is accelerated by an electric field formed between the retarding voltage and an electrode in the vicinity of the sample and an objective lens and the like. In the case of acceleration by an electric field formed between the sample and the objective lens of a ground potential, the secondary electron is accelerated toward the direction of the electron source by energy of 2,000 eV.

Under such situation as above, if the desired charge quantity ($V_{pre}$) is +100 V, the acceleration energy of the secondary electron emitted from the sample when the desired charge quantity is obtained becomes $V_r+V_{pre}=1,900$ eV (when the secondary electron is almost 0 eV). In other words, if the energy of the electron emitted from the sample during pre-dose can be monitored, catching accurately the timing for stopping scanning for pre-dose becomes possible. If the voltage applied to the energy filter is set to the vicinity of −1,900 V, the secondary electron slowed down by 100 eV or more by pre-dose cannot pass through the energy filter. If the relation between the detected electron quantity and the charge quantity of pre-dose is known beforehand, it can be judged that the time when the detected electron quantity reaches a predetermined value is the time when the desired charge quantity is secured.

Those which can pass through the energy filter with the applied voltage of −1,900 V are only the electrons with the accelerating energy exceeding 1,900 eV. If charging of the sample proceeds by pre-dose, the acceleration energy of the electron emitted from the sample lowers gradually, therefore, the quantity of electrons that can pass through the energy filter decreases gradually.

If the control, such that, an electron quantity appropriate for stopping pre-dose is memorized beforehand relating to the combination of the optical condition (beam current, landing energy of the electron beam, magnification, and the like) when the applied voltage to the energy filter is made a predetermined value and the kind of the sample, and pre-dose is stopped when the electron quantity is reached, is performed, same charge condition can be realized stably regardless of the sample condition which is effective for improving the length measurement reproducibility. Further, measurement of charge is also performed in parallel with pre-dose which is effective for improving throughput.

Although above explanation describes an example wherein pre-dose and charge measurement proceed simultaneously, it is not necessary to limit to it, and, for example, both of them may be proceeded alternately in series like pre-dose→charge measurement→pre-dose→charge measurement→ . . . . In this case, pre-dose may be stopped by time control by plotting the change of the electron quantity with respect to change of time and predicting the timing when the predetermined electron quantity is reached by extrapolation.

What is claimed is:

1. A scanning electron microscope comprising:
   an electron source,
   a lens for converging an electron beam emitted from the electron source,
   a scanning deflector for scanning an electron beam on a sample, and
   a detector for detecting an electron emitted from the sample, wherein;
   a control device for controlling the lens and the scanning deflector is provided, and
   the control device controls the scanning deflector so that, after a first electron beam is scanned to the sample to charge it, a second electron beam scans within the charged region to detect an electron emitted from the sample, and controls the lens so that the beam diameter of the first electron beam becomes larger than the beam diameter of the second electron beam.

2. The scanning electron microscope as set forth in claim 1, wherein
   the control device controls the scanning deflector so that the beam diameter of the first electron beam becomes equal to or larger than the distance between scanning lines of the first electron beam.

3. The scanning electron microscope as set forth in claim 1, wherein
   the control device controls the beam diameter by lens strength of a lens for converging the electron beam.

4. The scanning electron microscope as set forth in claim 3, wherein
   the lens is an objective lens and the control device adjusts the beam diameter by controlling an excitation amount of the objective lens.

* * * * *